(12) United States Patent
Kalpana et al.

(10) Patent No.: US 8,460,635 B2
(45) Date of Patent: Jun. 11, 2013

(54) FENRETINIDE DERIVATIVES AND USES THEREOF AS THERAPEUTIC, DIAGNOSTIC AND IMAGING AGENTS

(75) Inventors: Ganjam V. Kalpana, Yonkers, NY (US); Bhaskar C. Das, West Nyack, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 197 days.

(21) Appl. No.: 12/735,544

(22) PCT Filed: Mar. 11, 2009

(86) PCT No.: PCT/US2009/001538
§ 371 (c)(1),
(2), (4) Date: Dec. 13, 2010

(87) PCT Pub. No.: WO2009/114136
PCT Pub. Date: Sep. 17, 2009

(65) Prior Publication Data
US 2011/0091383 A1    Apr. 21, 2011

Related U.S. Application Data

(60) Provisional application No. 61/069,050, filed on Mar. 12, 2008.

(51) Int. Cl.
*A61K 51/00* (2006.01)
*A61M 36/14* (2006.01)

(52) U.S. Cl.
USPC ......... 424/1.11; 424/1.89; 564/181; 564/123; 514/613; 514/502; 514/617; 556/138

(58) Field of Classification Search
None
See application file for complete search history.

(56) References Cited

U.S. PATENT DOCUMENTS

| | | |
|---|---|---|
| 4,532,343 A | 7/1985 | Dawson et al. |
| 7,169,813 B2 | 1/2007 | Formelli |
| 2003/0105164 A1 | 6/2003 | Curley, Jr. et al. |
| 2006/0167088 A1 | 7/2006 | Widder et al. |
| 2010/0183504 A1* | 7/2010 | Chen .......................... 424/1.29 |

* cited by examiner

*Primary Examiner* — Michael G Hartley
*Assistant Examiner* — Sean R Donohue
(74) *Attorney, Agent, or Firm* — Amster, Rothstein & Ebenstein LLP

(57) ABSTRACT

Synthetic peptidomimetic derivatives and phenyl group derivatives of Fenretinide (4-HPR) are disclosed, as are their uses as therapeutic, diagnostic and imaging agents for cancer and other diseases.

14 Claims, 6 Drawing Sheets

A.

B.

FENRETINIDE DERIVATIVES AND USES THEREOF AS THERAPEUTIC, DIAGNOSTIC AND IMAGING AGENTS

CROSS-REFERENCE TO RELATED APPLICATIONS

This application is a national stage entry under 35 U.S.C. §371 of PCT International Patent Application No. PCT/US2009/001538, filed Mar. 11, 2009, and claims priority to U.S. Provisional Patent Application No. 61/069,050, filed Mar. 12, 2008, the contents of which are incorporated herein by reference in their entirety into the subject application.

FIELD OF THE INVENTION

The present invention relates to synthetic derivatives of Fenretinide (4-HPR) and their uses as therapeutic, diagnostic and imaging agents for cancer and other diseases.

BACKGROUND OF THE INVENTION

Throughout this application various publications are referred to in parenthesis. Citations for these references may be found at the end of the specification immediately preceding the claims. The disclosures of these publications are hereby incorporated by reference in their entireties into the subject application to more fully describe the art to which the subject application pertains.

Fenretinide and its Significance in Clinical and Biological Studies:

4-HPR [N-(4-hydroxyphenyl)retinamide, or Fenretinide] is a synthetic retinoid that has potent chemopreventive and antiprolliferative effects against many cancers in vitro and in preclinical models, and it does not show appreciable side effects. It exhibits cytotoxicity and in vitro suppresses tumor cell growth at low micromolar concentrations (IC50s) ranging from 1-10 µM (1). 4-HPR is an FDA approved drug under phase II clinical trials for many cancers including neuroblastomas, currently sponsored by the National Cancer Institute (Ref: 06-C-0227). Fenretinide has been largely studied as a chemo-preventive agent in carcinogen-induced epithelial tumors in animal models and in patients at risk for breast cancer (2-5). In advanced metastatic breast cancer, 4HPR has minimal activity; however, in comparison to other retinoids, has low toxicity (2-4). However, recent results of a fifteen-year follow up studies of Phase III trials of Fenretinide to prevent second breast cancer indicated that it has significant risk reduction in premenopausal women, which is remarkable at younger age, and persists after several years (6). These studies indicate that Fenretinide has promising preventive activity in clinical trials of breast cancer. In pediatric neuroblastoma patients, use of 4HPR has demonstrated prolonged stabilization of disease in pilot clinical studies (7-10).

4HPR induces apoptosis in tumor cell lines in vitro by various mechanisms including: (i) activation of retinoid receptors RAR β and γ; (ii) induction of ceramide-dependent cell cytotoxicity that is independent of p53 or caspase-3 function and thus is synergistic with tamoxifen, which in turn is an inhibitor of glucosylceramide synthase; (iii) generation of free radical oxygen species; (iv) increase of NOS expression resulting in increased NO-dependent cell cytotoxicity; and (v) increase of mitochondrial permeability transition (2, 4, 7, 8, 10). 4HPR also induces cell cycle arrest and down modulates the expression or activity of proliferation related targets such as c-myc, telomerase, p34/cdc2 and Cyclin (10-21). These effects correlate with the induction of phosphorylation of Rb, cell cycle arrest and subsequent induction of apoptosis.

Over-expression of CyclinD1 is sufficient to sensitize certain cancer cells to 4-HPR, indicating that CyclinD1 may be a key cellular target for the action of this drug (22). Consistent with this idea, 4-HPR appears to affect the expression as well as the protein stability of cyclin D1 in a concentration dependent manner (23-26), and in leukemia cell lines, efficacy of 4HPR correlates with CyclinD1 depletion.

This information about the ability of Fenretinide to target Cyclin D1 was used to inhibit rhabdoid tumors, which are highly malignant pediatric tumors (27). Previous studies conducted at Albert Einstein College of Medicine indicated that rhabdoid cells over-express CyclinD1, and that these cells are critically dependent on Cyclin D1, using both in vitro cell culture models and in vivo genetically engineered mouse (GEM) models of rhabdoid tumors that are heterozygous for Ini1 locus (28-30). Based on these studies it was surmised that rhabdoid cells might be sensitive to 4HPR. Consistent with this hypothesis, it was established that rhabdoid tumors indeed are sensitive to 4-HPR in vitro and in vivo and its effect is correlated to down-modulation of Cyclin D1 (28).

4-HPR as a Therapeutic Agent for Diseases Other than Cancer:

4-HPR is a retinoid and as such it is likely to interfere with the retinoic acid pathway in the cells and affect the biology of the pathway. Since defects in retinoic acid synthesis, metabolism, and transcriptional regulation of downstream genes by its ability to bind to nuclear receptors (RAR and RXR) are important for growth, development, behaviour, and disease pathways (31-37), retinoic acid metabolism inhibitors are widely used as therapeutic agents in many diseases (38).

Fenretinide is a synthetic retinoid that induces apoptosis in cancer cells as opposed to retinoic acid and other retinoids that induce differentiation (4). Because of this reason, and because of its low toxicity and effect on many different pathways including ceramide biosynthesis, free radical oxygen, and NOS, Fenretinide has been widely investigated as a preventive or therapeutic agent in many diseases. In addition to cancer, several preclinical studies have suggested activity of this compound against an array of diseases including but not limited to diabetes, AIDS, Alzheimer's Disease, cystic fibrosis, allergic encephalomyelitis, and ichthyosis (4, 39-61).

4-HPR Analogues in Inducing Cytotoxicity:

4-HPR is one of the most widely investigated synthetic retinoids for cancer prevention, especially for breast cancer. Pharmacological studies in human clinical trials of breast cancer patients have revealed accumulation of plasma concentration of 4-HPR at 1 µM levels with administration of 200 mg/day (MTD) of 4-HPR (3). It is possible that a molar concentration higher than currently attainable within the tumors may be required to achieve desired cytocidal effect with 4-HPR in other human cancers. Additional studies have indicated that in vitro activity of Fenretinide does not match a correspondent efficacy in vivo, indicating a need for further improvement of the drug. Many reasons has been proposed to explain the discrepancy between in vitro and in vivo activities of the drug, including decreased bioavailability and inability of the drug to cross the blood-brain barrier. The lack of bioavailability could be due to the hydrophobicity of the drug, where it never reaches amounts suitable for therapeutic response within the tumors. One report indicated the development of 4-HPR linked to polyvinylalcohol (PVA) (62). These studies indicated the feasibility of linking Fenretinide to improve its bioavailability.

There are few studies where synthetic analogues of 4-HPR have been reported to be active in cell toxicity studies. For example, it was reported that a non-hydrolysable carbon linked analogue of 4-HPR (N-benzyl hydroxyl retinamide, 4-HBR), potentially reduces suppression of plasma vitamin A levels (63, 64). The sulfur-containing heteroretinoids induce apoptosis and reactive oxygen species specifically in malignant but not in benign cells (65). Conjugations of 4-HPR also have been reported to be effective in antitumor activity. It was reported that anti-tumor potency of 4-HPR increases when it was conjugated to glucuronides. Glycosyl conjugated mannosyl with 4-HPR increased activity on promyelocytic leukemia cell lines HL60 (66). Recently, it was reported that 4-Oxo-fenretinide induced marked G2-M cell cycle arrest and apoptosis in fenretinide-sensitive and fenretinide resistant cell lines (67). Thus, there continues to be a need for improved 4-HPR derivates that demonstrate more potent biological activity efficacy and improved bioavailability and ability to cross the blood brain-barrier compared to parent 4-HPR.

SUMMARY OF THE INVENTION

The invention provides a compound having the formula:

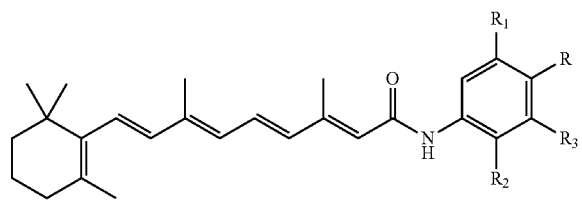

wherein R is OH; wherein $R_1$, $R_2$ and $R_3$ are independently H, Br, Cl, I, F, alkyl, aryl, OH, $NO_2$, $NHR_4$, $OR_4$ or heterocyclic, where $R_4$ is alkyl, aryl or heterocyclic, and where at least one of $R_1$, $R_2$ and $R_3$ is not H; or a pharmaceutically acceptable salt thereof.

The invention also provides a compound having the formula:

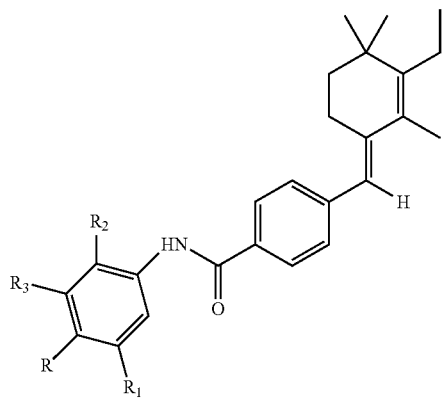

wherein R is OH; wherein $R_1$, $R_2$ and $R_3$ are independently H, Br, Cl, I, F, alkyl, aryl, OH, $NO_2$, $NHR_4$, $OR_4$ or heterocyclic, where $R_4$ is alkyl, aryl or heterocyclic; or a pharmaceutically acceptable salt thereof.

The invention also provides a pharmaceutical composition comprising a compound of the present invention and a pharmaceutically acceptable carrier or diluent.

The invention further provides a method of treating a subject having a cancer comprising administering to the subject a compound of the present invention in an amount and manner effective to treat cancer in the subject.

The invention further provides a method of treating a subject having a disease comprising administering to the subject a compound of the present invention in an amount and manner effective to treat the disease in the subject.

DETAILED DESCRIPTION OF THE INVENTION

Figures 1A, 1B:
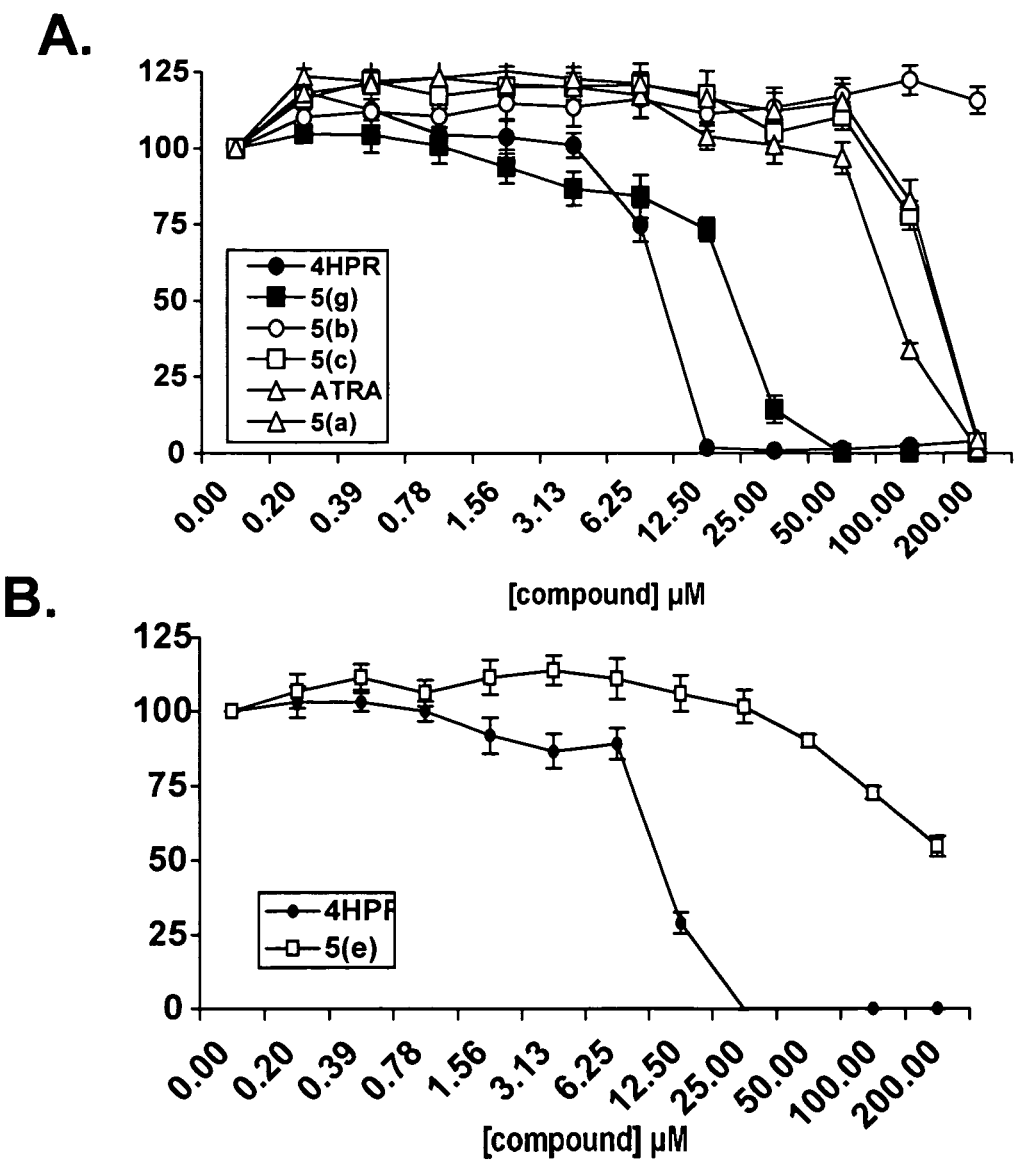
FIG. 1A-1D. Effect of 4HPR derivatives with phenyl group substitutions on survival of rhabdoid tumors cells. MON (INI1−/−) cells were treated with serial dilutions of the 4HPR, ATRA and 4HPR derivatives for three days. Survival assay was carried out as described using MTS assay kit. Percentage of cell survival plotted against concentration of drugs (Mean+/−SEM).

The invention provides a compound having the formula:

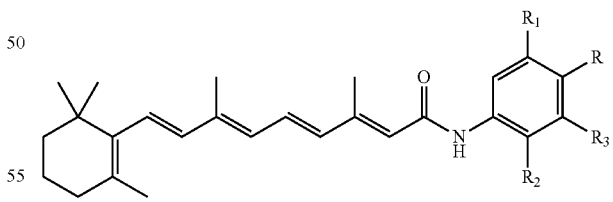

wherein R is OH; wherein $R_1$, $R_2$ and $R_3$ are independently H, Br, Cl, I, F, alkyl, aryl, OH, $NO_2$, $NHR_4$, $OR_4$ or heterocyclic, where $R_4$ is alkyl, aryl or heterocyclic, and where at least one of $R_1$, $R_2$ and $R_3$ is not H; or a pharmaceutically acceptable salt thereof Preferably, at least one of $R_1$, $R_2$ and $R_3$ is OH, Br, Cl, I or F; and at least one of $R_1$, $R_2$ and $R_3$ is H. Preferably, at least one of $R_1$ and $R_3$ is Br, Cl, I or F. Most preferably, $R_3$ is I. Preferably, $R_2$ is H or OH.

Preferred compounds include, but are not limited to, compounds selected from the group consisting of:

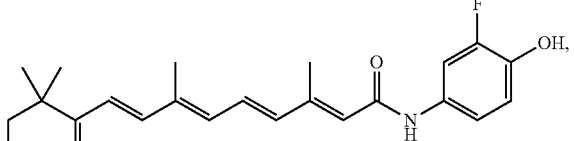
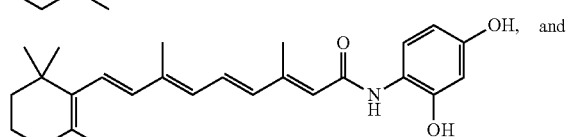
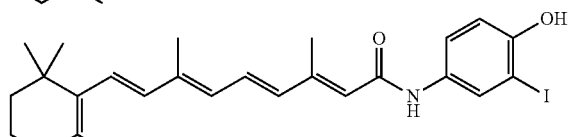
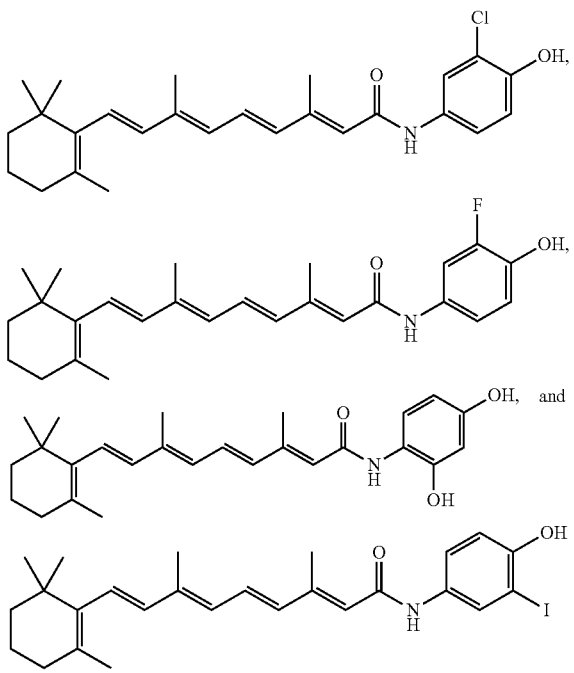

or a pharmaceutically acceptable salt thereof

More preferably, the compound is:

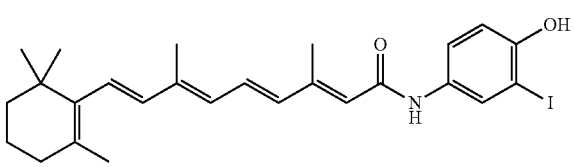 [SMILES: CC1=C(/C=C/C(C)=C/C=C/C(C)=C/C(=O)Nc2ccc(O)c(I)c2)C(C)(C)CCC1]

or a pharmaceutically acceptable salt thereof

The invention also provides a compound having the formula:

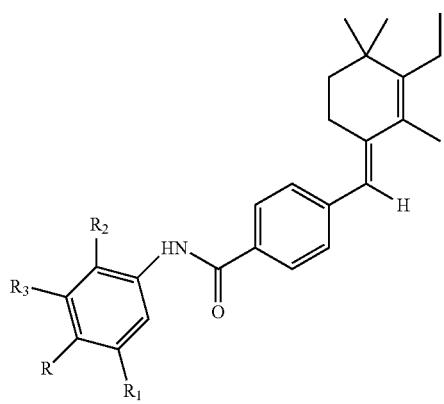

wherein R is OH; wherein $R_1$, $R_2$ and $R_3$ are independently H, Br, Cl, I, F, alkyl, aryl, OH, $NO_2$, $NHR_4$, $OR_4$ or heterocyclic, where $R_4$ is alkyl, aryl or heterocyclic; or a pharmaceutically acceptable salt thereof Preferably, at least one of $R_1$, $R_2$ and $R_3$ is OH, Br, Cl, I or F; and at least one of $R_1$, $R_2$ and $R_3$ is H. Preferably, at least one of $R_1$ and $R_3$ is Br, Cl, I or F. Most preferably, $R_3$ is I. Preferably, $R_2$ is H or OH.

Preferred compounds include, but are not limited to, compounds selected from the group consisting of:

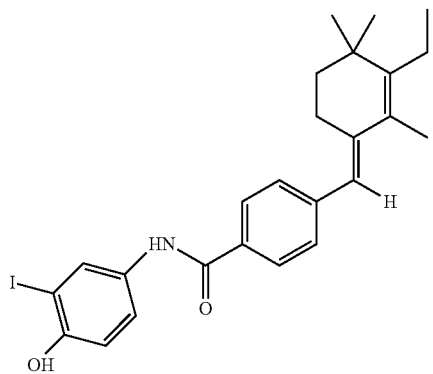 [SMILES: CCC1=C(C)/C(=C/c2ccc(C(=O)Nc3ccc(O)c(I)c3)cc2)CCC1(C)C]

or a pharmaceutically acceptable salt thereof.

More preferably, the compound is:

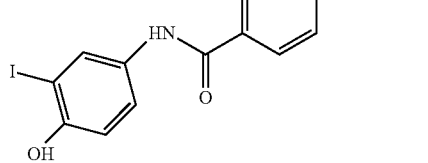

or a pharmaceutically acceptable salt thereof.

Pharmaceutically acceptable salts are non-toxic salts derived for example from inorganic or organic acids including, but not limited to, salts derived from hydrochloric, sulfuric, phosphoric, acetic, lactic, fumaric, succinic, tartaric, gluconic, citric, methanesulphonic and p-toluenesulphonic acids.

The compounds of the present invention can be radiolabeled. Preferred radiolabels include, but are not limited to, F-18, Cl-34 m, Br-75, Br-76, I-120, I-122, I-123, I-124, I-125 and I-131.

The compound of the present invention can be conjugated to a nanoparticle. Preferably, the nanoparticle is conjugated to the compound at position R, $R_1$, $R_2$ or $R_3$.

Preferably, the compounds of the present invention have improved efficacy, bioavailability and/or ability to cross the blood-brain barrier compared to N-(4-hydroxyphenyl)retinamide (4-HPR).

The invention also provides a pharmaceutical composition comprising a compound of the present invention and a pharmaceutically acceptable carrier or diluent. Pharmaceutically acceptable carriers and diluents encompasses any of the standard pharmaceutical carriers or diluents, such as, for example, a sterile isotonic saline, phosphate buffered saline solution, water and emulsions, such as an oil/water or water/oil emulsions.

The invention further provides a method of treating a subject having a cancer comprising administering to the subject a compound of the present invention in an amount and manner effective to treat cancer in the subject. Preferred forms of cancer include, but are not limited to, breast cancer, a rhabdoid tumor, a neuroblastoma, ovarian cancer, renal cancer, a malignant glioma and prostrate cancer.

The invention further provides a method of treating a subject having a disease comprising administering to the subject a compound of the present invention in an amount and manner effective to treat the disease in the subject. Preferred diseases include, but are not limited to, diabetes, AIDS, Alzheimer's Disease, cystic fibrosis, allergic encephalomyelitis and ichthyosis.

The compounds of the present invention can be administered to subjects using routes of administration known in the art. The administration can be systemic or localized to a tumor site. Routes of administration include, but are not limited to, intravenous, intramuscular, intrathecal or subcutaneous injection, oral or rectal administration, and injection into a tumor site.

The invention also provides for the use of any of the compounds disclosed herein for treating a subject with cancer or other disease, and for the use of any of the compounds disclosed herein for the preparation of a medicament for treatment of cancer or other disease. The invention further provides pharmaceutical compositions comprising any of the compounds disclosed herein for treatment of cancer or other disease.

The invention also provides a method of screening for compounds that inhibit tumor cell growth, the method comprising determining whether or not a compound down modulates Cyclin D1 and/or causes G1 cell cycle arrest, wherein a compound that down modulates Cyclin D1 and/or causes G1 cell cycle arrest is a candidate compound for inhibiting tumor cell growth and wherein a compound that does not down modulate Cyclin D1 and/or cause G1 cell cycle arrest is not a candidate compound for inhibiting tumor cell growth.

This invention will be better understood from the Experimental Details, which follow. However, one skilled in the art will readily appreciate that the specific methods and results discussed are merely illustrative of the invention as described more fully in the claims that follow thereafter.

Experimental Details

Introduction

Peptidomimetic Derivatives, Nanoparticle Conjugates and Radio-Labeled Derivatives and their Significance:

A chemical biology approach was undertaken to synthesize new peptidomimetic and functionalized derivatives of 4-HPR molecules to improve the efficacy, bioavailability and ability to cross the blood-brain barrier. Furthermore, a chemical synthesis approach was undertaken to synthesize radioconjugates of 4-HRP to facilitate diagnostic, pharmacokinetic studies and to combine chemotherapy with radiotherapy using a single drug.

Peptidomimetics, in broad terms, refer to molecules bearing identifiable resemblance to peptides that as a ligand of a biological receptor can imitate or inhibit the effect of a natural peptide (68-71). Peptidomimetics are superior to natural or synthetic peptides as therapeutic agents because they: (i) are less susceptible to proteolytic degradation; (ii) are better absorbed through the cell membrane; (iii) are transported across the blood-brain barrier efficiently; and/or (iv) because of their rigidity, exhibit specificity in their interaction with biological molecules. Peptidomimetics are designed by altering the amide bond of a compound and are further modified by cyclization, isostere replacement and changing the scaffold. Compounds that are not necessarily peptides but have amide bonds within their structures can also be modified based on these principles to improve their properties such as efficacy, solubility, bioavailability and/or transport.

Nanoscience and nanotechnology refer to research at the atomic, molecular or macromolecular levels, at the length scale of approximately 1-100 nanometers. The emerging goal of the nanotechnology is to functionalize inert and biocompatible materials to impart precise biological functions. To achieve these objectives new materials have been synthesized and tested for diagnostic and therapeutic agents including quantum dots, polymers and magnetofluorescent nanoparticles (72-83).

The union between nanotechnology and small molecule chemistry can facilitate development of a wide range of nanomaterials for biomedical applications as diagnostic and therapeutic agents. Another promising technique developed based on nanotechnology is the nanodrug and/or gene delivery system. This new technology provides greater potential for many applications, including anti-tumor therapy by targeted delivery of therapeutic agents to tumors. Cancer treatment represents an enormous biomedical challenge for drug delivery. The unique properties of cancer require the development of a multifunctional drug delivery system that can be efficiently manufactured to target subtle molecular alterations that distinguish a cancer cell from healthy cells in the body. A nanoparticle-mediated drug delivery system can significantly eliminate drug or drug carrier side effects.

Furthermore, a chemical synthesis approach was also undertaken to derive iodo- and flouro-derivatives of fenretinide that retain the biological activity of parent compound. By synthesizing of radio-labeled derivatives (F-18 and I-124) and combining with the powerful application of PET, the bio-distribution of this molecule can be analyzed in vivo. Furthermore, development of novel radio-labeled compounds of Fenretinide could potentially be useful for early detection and diagnosis of many malignancies including rhabdoid tumors, neuroblastoma, and breast cancer. Finally, deriving I-131 labeled compounds may potentially be useful as a radio-molecular therapeutic agent in rhabdoid tumors and a wide variety of adult as well as pediatric malignancies including breast, neuroblastoma, colon and ovarian.

Novel Fenretinide Derivatives and their Activity:

The purposes of the present studies include: first, chemically synthesize small and defined libraries of Fenretinide conjugates and derivatives; second, identify active molecules by using biologically relevant assays; and third, using the principles of peptdomimetics and nanoscience, modify these compounds further for the purpose of improving bioavailability, stability and ability to cross the blood-brain barrier. These molecules were screened using well-established rhabdoid tumor preclinical models, developed at Albert Einstein College of Medicine, to identify more active modified Fenretinide derivatives.

The active moiety required for the biological activity of 4-HPR was identified herein by generating a set of substitution derivatives in the phenyl ring. Furthermore, novel compounds that retain the effectiveness to inhibit thabdoid tumor cells were herein identified using in vitro cell culture assays, in a high-throughput liquid-handler robotics. In addition, the principle of peptidomimetics was used to generate various 4-HPR derivatives and using these systems, identify peptidomimetic derivatives of 4-HPR that show improved efficacy in cell survival assays of rhabdoid tumor cells. Identifying the active moiety, and active substitution derivations of Fenretinides have provided methods to conjugate Fenretinide to nanoparticles. The synthesis of active iodo-derivatives of Fenretinide that exhibit improved biological activity is also disclosed. These iodo-substitutions allow one to use radiolabeled 4-HPR to combine the chemotherapeutic potential with radiotherapy to increase the potency of 4-HPR. These conjugates could also be used as imaging probes to monitor the bio-distribution and in image-guided efficacy studies in preclinical models. Further, the activity of Fenretinide was shown to correlate with its ability to affect the biomarker expression, i.e. repression of Cyclin D1, using chemically modified active and inactive derivatives of Fenretinide.

Example I

Synthesis of Compounds

4-HPR derivatives were synthesized by changing the functional group in para and meta position of benzene ring systems. Iodo- and other halogen derivatives were obtained for combining radiotherapy with chemotherapy. Once the position required for retaining the biological activity was identified, the Retinoic acid backbone was then modified. In addition, peptidomimetic compounds were synthesized.

Fenretinamide Derivatives With Phenyl Group Substitutions

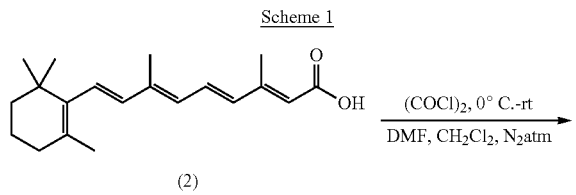

Scheme 1

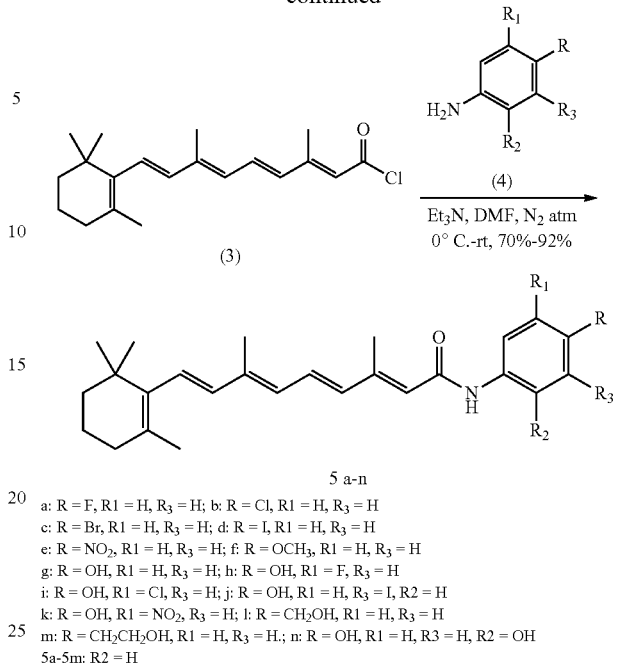

5 a-n
a: R = F, R1 = H, R$_3$ = H; b: R = Cl, R1 = H, R$_3$ = H
c: R = Br, R1 = H, R$_3$ = H; d: R = I, R1 = H, R$_3$ = H
e: R = NO$_2$, R1 = H, R$_3$ = H; f: R = OCH$_3$, R1 = H, R$_3$ = H
g: R = OH, R1 = H, R$_3$ = H; h: R = OH, R1 = F, R$_3$ = H
i: R = OH, R1 = Cl, R$_3$ = H; j: R = OH, R1 = H, R$_3$ = I, R2 = H
k: R = OH, R1 = NO$_2$, R$_3$ = H; l: R = CH$_2$OH, R1 = H, R$_3$ = H
m: R = CH$_2$CH$_2$OH, R1 = H, R$_3$ = H.; n: R = OH, R1 = H, R3 = H, R2 = OH
5a-5m: R2 = H

Experimental Procedures

All-trans retinoic acid (ATRA) was purchased from Sigma Chemical Co. (Sigma-Aldrich). The dry DMF was stored over 4-Å sieves and degassed before use by bubbling nitrogen through it for at least 1 h. The other reagents and solvents were purchased from commercially available sources (Aldrich and Fisher) and used without further purification. All reactions were conducted under a N$_2$ atmosphere. The reactions were monitored using TLC (Whatman® PE SIL G/UV Fluorescence UV$_{254}$). All the products prepared were purified by flash column chromatography on silica gel grade 62 (60-200 mesh, 150 Å). Proton nuclear magnetic resonance ($^1$H-NMR) were recorded in CDCl$_3$ using a Bruker 300 MHz instrument. Electrospray Ionization (ESI) mass spectra were determined on a Thermo Finnigan LCQ Classic ion trap mass spectrometer (Waltham, Mass.) in positive ionization mode.

(2E,4E,6E,8E)-[3,7-Dimethyl-9-(2,6,6-trimethyl-1-cyclohexenyl)-nona-2,4,6,8-tetraenoylamino]-(4-fluoro)phenylamide (5a in Scheme 1)

A mixture of all-trans retinoic acid (ATRA) (500 mg, 1.65 mmol) in dry DMF (5 mL) and dry CH$_2$Cl$_2$ (8 mL) was stirred under nitrogen atmosphere for 1 h. Oxalyl chloride (4.992 mmol, 4294) was added drop by drop at 0° C. The deep red reaction mixture was stirred for another 1.5 h at room temperature under nitrogen atmosphere. The solvent was very carefully removed, then dry DMF (5 mL) was added for immediate use. At 0° C. under nitrogen atmosphere, Retinoyl chloride solution was added dropwise to a solution of 4-fluoroaniline (3.328 mmol, 729 mg) and triethylamine (5 mmol, 694 µL) in dry DMF (5 mL). The dark-colored reaction mixture was stirred at room temperature and progress of the reaction was monitored using TLC. After the reaction completed 3.5 h, the reaction was quenched with saturated NH$_4$Cl and extracted with ethyl acetate (3×50 mL). The extracts were washed with H$_2$O (2×30 mL) and brine (2×20 mL), then dried overage Na$_2$SO$_4$, and evaporated. The residue was purified by flash column chromatography using hexane:ethyl acetate (98:

2) as the eluent to give a yellow solid. 1H-NMR(300 MHz, CDCl$_3$): δ7.53 (d, 2H), 7.05 (dd, 2H), 6.49~6.12 (m, 4H), 5.80 (s, 1H), 2.44 (s, 3H), 2.03 (br s, 5H), 1.74 (s, 3H), 1.54~1.45 (m, 2H), 1.32 (s, 2H), 1.27 (s, 2H), 1.05 (s, 6H). ESI MS: [M+H]$^+$394.13, calcd M 393.25 for C$_{26}$H$_{32}$FNO.

(2E,4E,6E,8E)-[3,7-Dimethyl-9-(2,6,6-trimethyl-1-cyclohexenyl)-nona-2,4,6,8-tetraenoylamino]-(4-chloro)phenylamide (5b in Scheme 1)

A mixture of all-trans retinoic acid (ATRA) (100 mg, 0.33 mmol) in dry DMF (1 mL) and dry CH$_2$Cl$_2$ (1.5 mL) was stirred under nitrogen atmosphere for 1 h. Oxalyl chloride (1.25 mmol, 108 μL) was added drop by drop at 0° C. The deep red reaction mixture was stirred for another 1.5 h at room temperature under nitrogen atmosphere. The solvent was very carefully removed, then dry DMF (2 mL) was added for immediate use. At 0° C. under nitrogen atmosphere, Retinoyl chloride solution was added dropwise to a solution of 4-chloroaniline (0.666 mmol, 86 mg) and triethylamine (1.000 mmol, 140 μL) in dry DMF (1 mL). The dark-colored reaction mixture was stirred at room temperature and progress of the reaction was monitored using TLC. After the reaction completed 3.5 h, the reaction was quenched with saturated NH$_4$Cl (8 mL) and extracted with ethyl acetate (2×15 mL). The extracts were washed with (2×10 mL) and brine (2×10 mL), then dried overage Na$_2$SO$_4$, and evaporated. The residue was purified by flash column chromatography using hexane:ethyl acetate (94:6) as the eluent to give a yellow solid. 1H-NMR (300 MHz, CDCl$_3$): δ7.50 (d, 2H), 7.03 (dd, 2H), 6.33~6.19 (m, 4H), 5.80 (s, 1H), 2.45 (s, 3H), 2.04 (br s, 5H), 1.74 (s, 3H), 1.51~1.49 (m, 2H), 1.33 (s, 2H), 1.27 (s, 2H), 1.05 (s, 6). ESI MS: [M+H]$^+$410.13, calcd M 409.22 for C$_{26}$H$_{32}$ClNO.

(2E,4E,6E,8E)-[3,7-Dimethyl-9-(2,6,6-trimethyl-1-cyclohexenyl)-nona-2,4,6,8-tetraenoylamino]-(4-bromo)phenylamide (5c in Scheme 1)

A mixture of all-trans retinoic acid (ATRA) (100 mg, 0.33 mmol) in dry DMF (1 mL) and dry CH$_2$Cl$_2$ (3 mL) was stirred under nitrogen atmosphere for 1 h. Oxalyl chloride (1.25 mmol, 108 μL) was added drop by drop at 0° C. The deep red reaction mixture was stirred for another 1.5 h at room temperature under nitrogen atmosphere. The solvent was very carefully removed, then dry DMF (2 mL) was added for immediate use. At 0° C. under nitrogen atmosphere, Retinoyl chloride solution was added dropwise to a solution of 4-bromoaniline (0.666 mmol, 115 mg) and triethylamine (1.000 mmol, 140 mL) in dry DMF (1 mL). The dark-colored reaction mixture was stirred at room temperature and progress of the reaction was monitored using TLC. After the reaction completed 3.5 h, the reaction was quenched with saturated NH$_4$Cl (8 mL) and extracted with ethyl acetate (2×15 mL). The extracts were washed with H$_2$O (2×10 mL) and brine (2×10 mL), then dried overage Na$_2$SO$_4$, and evaporated. The residue was purified by flash column chromatography using hexane:ethyl acetate (98:2) as the eluent to give a yellow solid. 1H-NMR(300 MHz, CDCl$_3$): δ7.67 (d, 2H), 7.47 (dd, 2H), 6.49~6.12 (m, 4H), 5.79 (s, 1H), 2.44 (s, 3H), 2.03 (br s, 5H), 1.74 (s, 3H), 1.50 (m, 2H), 1.33 (m, 2H), 1.27 (m, 2H), 1.05 (s, 6H).

(2E,4E,6E,8E)-[3,7-Dimethyl-9-(2,6,6-trimethyl-1-cyclohexenyl)-nona-2,4,6,8-tetraenoylamino]-(4-iodo)phenylamide (5d in Scheme 1)

A mixture of all-trans retinoic acid (ATRA) (500 mg, 1.65 mmol) in dry DMF (5 mL) and dry CH$_2$Cl$_2$ (8 mL) was stirred under nitrogen atmosphere for 1 h. Oxalyl chloride (4.992 mmol, 429 μL) was added drop by drop at 0° C. The deep red reaction mixture was stirred for another 1.5 h at room temperature under nitrogen atmosphere. Very carefully removed the solvent, then added dry DMF (5 mL) for immediate use. At 0° C. under nitrogen atmosphere, Retinoyl chloride solution was added dropwise to a solution of 4-iodoaniline (3.328 mmol, 729 mg) and triethylamine (5 mmol, 694 μL) in dry DMF (5 mL). The dark-colored reaction mixture was stirred at room temperature and progress of the reaction was monitored using TLC. After the reaction completed 3.5 h, the reaction was quenched with saturated NH$_4$Cl and extracted with ethyl acetate (3×50 mL). The extracts were washed with H$_2$O (2×30 mL) and brine (2×20 mL), then dried overage Na$_2$SO$_4$, and evaporated. The residue was purified by flash column chromatography using hexane:ethyl acetate (98:2) as the eluent to give a yellow solid. 1H-NMR (300 MHz, CDCl$_3$): δ7.52 (d, 2H), 7.04 (dd, 2H), 6.51~6.11 (m, 4H), 5.80 (s, 1H), 2.45 (s, 3H), 2.03 (br s, 5H), 1.74 (s, 3H), 1.54~1.47 (m, 2H), 1.32 (s, 2H), 1.27 (s, 2H), 1.05 (s, 6H).

(2E,4E,6E,8E)-[3,7-Dimethyl-9-(2,6,6-trimethyl-1-cyclohexenyl)-nona-2,4,6,8-tetraenoylamino]-(4-nitro)phenylamide (5e in Scheme 1)

A mixture of all-trans retinoic acid (ATRA) (100 mg, 0.33 mmol) in dry DMF (1 mL) and dry CH$_2$Cl$_2$ (3 mL) was stirred under nitrogen atmosphere for 1 h. Oxalyl chloride (1.25 mmol, 108 μL) was added drop by drop at 0° C. The deep red reaction mixture was stirred for another 1.5 h at room temperature under nitrogen atmosphere. Very carefully removed the solvent, then added dry DMF (2 mL) for immediate use. At 0° C. under nitrogen atmosphere, Retinoyl chloride solution was added dropwise to a solution of 4-nitroaniline (0.666 mmol, 92 mg) and triethylamine (1.000 mmol, 140 μL) in dry DMF (1 mL). The dark-colored reaction mixture was stirred at room temperature and progress of the reaction was monitored using TLC. After the reaction completed 3.5 h, the reaction was quenched with saturated NH$_4$Cl (8 mL) and extracted with ethyl acetate (2×15 mL). The extracts were washed with H$_2$O (2×10 mL) and brine (2×10 mL), then dried overage Na$_2$SO$_4$, and evaporated. The residue was purified by flash column chromatography using hexane:ethyl acetate (98:2) as the eluent to give a yellow solid. 1H-NMR(300 MHz, CDCl$_3$): δ7.57 (d, 2H), 7.07 (dd, 2H), 6.40~6.07 (m, 4H), 5.82 (s, 1H), 2.43 (s, 3H), 2.03 (br s, 5H), 1.72 (s, 3H), 1.69~1.59 (m, 2H), 1.51 (m, 2H), 1.27 (s, 2H), 1.05 (s, 6H), (2E,4E,6E,8E)-[3,7-Dimethyl-9-(2,6,6-trimethyl-1-cyclohexenyl)-nona-2,4,6,8-tetraenoylamino]-(4-methoxy)phenylamide (5f in Scheme 1)

A mixture of all-trans retinoic acid (ATRA) (100 mg, 0.33 mmol) in dry DMF (1 mL) and dry CH$_2$Cl$_2$ (3 mL) was stirred under nitrogen atmosphere for 1 h. Oxalyl chloride (1.25 mmol, 108 μL) was added drop by drop at 0° C. The deep red reaction mixture was stirred for another 1.5 h at room temperature under nitrogen atmosphere. Very carefully removed the solvent, then added dry DMF (2 mL) for immediate use. At 0° C. under nitrogen atmosphere, Retinoyl chloride solution was added dropwise to a solution of p-anisidine (0.666 mmol, 82 mg) and triethylamine (1.000 mmol, 140 μL) in dry DMF (1 mL). The dark-colored reaction mixture was stirred at room temperature and progress of the reaction was monitored using TLC. After the reaction completed 3.5 h, the reaction was quenched with saturated NH$_4$Cl (8 mL) and extracted with ethyl acetate (2×15 mL). The extracts were washed with (2×10 mL) and brine (2×10 mL), then dried overage Na$_2$SO$_4$, and evaporated. The residue was purified by flash column chromatography using hexane:ethyl acetate (92:8) as the eluent to give a yellow solid. 1H-NMR(300 MHz, CDCl$_3$): δ7.48 (d, 2H), 7.05 (dd, 2H), 6.47~6.15 (m, 4H), 3.87 (s, 3H), 2.43 ((s, 3H), 2.06 (br s, 5H), 1.73 (s, 3H), 1.64 (m, 2H), 1.53 (m, 2H), 1.29 (m, 2H), 1.05 (s, 6H). ESI MS: [M+H]$^+$406.13, calcd M 405.27 for C$_{27}$H$_{35}$NO$_2$.

(2E,4E,6E,8E)-[3,7-Dimethyl-9-(2,6,6-trimethyl-1-cyclohexenyl)-nona-2,4,6,8-tetraenoylamino]-(4-hydroxy)phenylamide (4-HPR) (5 g in Scheme 1)

A mixture of all-trans retinoic acid (ATRA) (200 mg, 0.66 mmol) in dry DMF (2 mL) and dry CH$_2$Cl$_2$ (2 mL) was stirred under nitrogen atmosphere for 1 h. Oxalyl chloride (2.5 mmol, 215 µL) was added drop by drop at 0° C. The deep red reaction mixture was stirred for another 1.5 h at room temperature under nitrogen atmosphere. Very carefully removed the solvent, then added dry DMF (2 mL) for immediate use. At 0° C. under nitrogen atmosphere, Retinoyl chloride solution was added dropwise to a solution of 4-aminophenol (1.331 mmol, 145.3 mg) and triethylamine (1.997 mmol, 280 µL) in dry DMF (2 mL). The dark-colored reaction mixture was stirred at room temperature until TLC analysis indicated none remaining (about 2~3 h). The reaction was quenched with saturated NH$_4$Cl and extracted with ethyl acetate. The extracts were washed with H$_2$O and brine, then dried overage Na$_2$SO$_4$, and evaporated. The residue was purified by flash column chromatography using hexane/ethyl acetate (3/1) as the eluent to give 4-HPR as a yellow solid. 1H-NMR(300 MHz, CDCl$_3$): δ7.42 (d, 2H), 7.11 (s, 1H), 6.99 (dd, 1H), 6.83 (d, 2H), 6.33~6.18 (m, 4H), 5.80 (s, 1H), 2.44 (s, 3H), 2.04 (br s, 5H), 1.74 (s, 3H), 1.64~1.62 (m, 2H), 1.33 (m, 2H), 1.05 (s, 6H).

(2E,4E,6E,8E)-[3,7-Dimethyl-9-(2,6,6-trimethyl-1-cyclohexenyl)-nona-2,4,6,8-tetraenoylamino]-(3-fluoro,4-hydroxy)phenylamide (5 h in Scheme 1)

A mixture of all-trans retinoic acid (ATRA) (100 mg, 0.33 mmol) in dry DMF (1 mL) and dry CH$_2$Cl$_2$ (3 mL) was stirred under nitrogen atmosphere for 1 h. Oxalyl chloride (1.25 mmol, 108 µL) was added drop by drop at 0° C. The deep red reaction mixture was stirred for another 1.5 h at room temperature under nitrogen atmosphere. Very carefully removed the solvent, then added dry DMF (2 mL) for immediate use. At 0° C. under nitrogen atmosphere, Retinoyl chloride solution was added dropwise to a solution of 4-amino-2-fluorophenol (0.666 mmol, 85 mg) and triethylamine (1.000 mmol, 140 µL) in dry DMF (1 mL). The dark-colored reaction mixture was stirred at room temperature and progress of the reaction was monitored using TLC. After the reaction completed 3 h, The reaction was quenched with saturated NH$_4$Cl (8 mL) and extracted with ethyl acetate (2×15 mL). The extracts were washed with (2×10 mL) and brine (2×10 mL), then dried overage Na$_2$SO$_4$, and evaporated. The residue was purified by flash column chromatography using hexane:ethyl acetate (7:1) as the eluent to give a yellow solid. 1H-NMR (300 MHz, CDCl$_3$): δ9.61 (s, 1H), 7.69 (d, 1H), 7.15 (d, 1H), 6.967 (d, 1H), 6.31~6.14 (m, 4H), 5.77 (s, 1H), 5.12 (br s, 1H), 2.43 (s, 3H), 2.04 (br s, 5H), 1.74 (s, 3H), 1.62 (m, 2H), 1.49 (m, 2H), 1.05 (s, 6H). ESI MS: [M+H]$^+$410.07, calcd M 409.24 for C$_{26}$H$_{32}$FNO$_2$.

(2E,4E,6E,8E)-[3,7-Dimethyl-9-(2,6,6-trimethyl-1-cyclohexenyl)-nona-2,4,6,8-tetraenoylamino]-(3-chloro, 4-hydroxy)phenylamide (5l in Scheme 1)

A mixture of all-trans retinoic acid (ATRA) (100 mg, 0.33 mmol) in dry DMF (1 mL) and dry CH$_2$Cl$_2$ (3 mL) was stirred under nitrogen atmosphere for 1 h. Oxalyl chloride (1.25 mmol, 108 µL) was added drop by drop at 0° C. The deep red reaction mixture was stirred for another 1.5 h at room temperature under nitrogen atmosphere. Very carefully removed the solvent, then added dry DMF (2 mL) for immediate use. At 0° C. under nitrogen atmosphere, Retinoyl chloride solution was added dropwise to a solution of 4-amino-2-chlorophenol (0.666 mmol, 96 mg) and triethylamine (1.000 mmol, 140 µL) in dry DMF (1 mL). The dark-colored reaction mixture was stirred at room temperature and progress of the reaction was monitored using TLC. After the reaction completed 3 h, The reaction was quenched with saturated NH$_4$Cl (8 mL) and extracted with ethyl acetate (2×15 mL). The extracts were washed with (2×10 mL) and brine (2×10 mL), then dried overage Na$_2$SO$_4$, and evaporated. The residue was purified by flash column chromatography using hexane:ethyl acetate (5:1) as the eluent to give a yellow solid.

1H-NMR(300 MHz, CDCl$_3$): δ7.84 (s, 1H), 7.17 (d, 1H), 6.99 (dd, 2H), 6.31~6.18 (m, 4H), 5.77 (s, 1H), 5.44 (s, 1H), 2.44 (s, 3H), 2.03 (br s, 5H), 1.74 (s, 3H), 1.62 (m, 2H), 1.51 (m, 2H), 1.33 (m, 2H), 1.05 (s, 6H). ESI MS:[M+H]$^+$426.07, calcd M 425.21 for C$_{26}$H$_{32}$ClNO$_2$.

(2E,4E,6E,8E)-[3,7-Dimethyl-9-(2,6,6-trimethyl-1-cyclohexenyl)-nona-2,4,6,8-tetraenoylamino]-(3-Iodo, 4-hydroxy)phenylamide (5j in Scheme 1)

A mixture of all-trans retinoic acid (ATRA) (57 mg, 0.19 mmol) in dry DMF (1 mL) and dry CH$_2$Cl$_2$ (2 mL) was stirred under nitrogen atmosphere for 1 h. Oxalyl chloride (0.72 mmol, 62 µL) was added drop by drop at 0° C. The deep red reaction mixture was stirred for another 1.5 h at room temperature under nitrogen atmosphere. Very carefully removed the solvent, then added dry DMF (2 mL) for immediate use. At 0° C. under nitrogen atmosphere, Retinoyl chloride solution was added dropwise to a solution of 4-amino-2-iodophenol (0.38 mmol, 90 mg) and triethylamine (0.57 mmol, 80 µL) in dry DMF (2 mL). The dark-colored reaction mixture was stirred at room temperature until TLC analysis indicated none remaining (about 2~3 h). The reaction was quenched with saturated NH$_4$Cl and extracted with ethyl acetate. The extracts were washed with H$_2$O and brine, then dried overage Na$_2$SO$_4$, and evaporated. The residue was purified by flash column chromatography using hexane/ethyl acetate (8/1) as the eluent to give 5j as a yellow solid. 1H-NMR(300 MHz, CDCl$_3$): δ9.61 (s, 1H), 7.69 (d, 1H), 7.15 (d, 1H), 6.967 (d, 1H), 6.31~6.14 (m, 4H), 5.77 (s, 1H), 5.12 (br s, 1H), 2.43 (s, 3H), 2.04 (br s, 5H), 1.74 (s, 3H), 1.62 (m, 2H), 1.49 (m, 2H), 1.05 (s, 6H). ESI MS:[M+]$^+$518.05, calcd M 517.15 for C$_{26}$H$_{32}$INO$_2$.

(2E,4E,6E,8E)-[3,7-Dimethyl-9-(2,6,6-trimethyl-1-cyclohexenyl)-nona-2,4,6,8-tetraenoylamino]-(3-nitro, 4-hydroxy)phenylamide (5k in Scheme 1)

A mixture of all-trans retinoic acid (ATRA) (100 mg, 0.33 mmol) in dry DMF (1 mL) and dry CH$_2$Cl$_2$ (3 mL) was stirred under nitrogen atmosphere for 1 h. Oxalyl chloride (1.25 mmol, 108 µL) was added drop by drop at 0° C. The deep red reaction mixture was stirred for another 1.5 h at room temperature under nitrogen atmosphere. Very carefully removed the solvent, then added dry DMF (2 mL) for immediate use. At 0° C. under nitrogen atmosphere, Retinoyl chloride solution was added dropwise to a solution of 4-amino-2-nitrophenol (0.666 mmol, 103 mg) and triethylamine (1.000 mmol, 140 µL) in dry DMF (1 mL). The dark-colored reaction mixture was stirred at room temperature and progress of the reaction was monitored using TLC. After the reaction completed 2 h, The reaction was quenched with saturated NH$_4$Cl (8 mL) and extracted with ethyl acetate (2×15 mL). The extracts were washed with (2×10 mL) and brine (2×10 mL), then dried overage Na$_2$SO$_4$, and evaporated. The residue was purified by flash column chromatography using hexane:ethyl acetate (93:7) as the eluent to give a yellow solid. 1H-NMR (300 MHz, CDCl$_3$): δ10.47 (s, 1H), 8.38 (s, 1H), 7.79 (d, 1H), 7.17 (d, 2H), 6.33~6.14 (m, 4H), 5.78 (s, 1H), 2.46 (s, 3H), 2.04 (br s, 6H), 1.74 (s, 3H), 1.61~1.51 (m, 6H), 1.06 (s, 6H). ESI MS:[M+H]$^+$437.13, calcd M 436.24 for C$_{26}$H$_{32}$N$_2$O$_4$.

(2E,4E,6E,8E)-[3,7-Dimethyl-9-(2,6,6-trimethyl-1-cyclohexenyl)-nona-2,4,6,8-tetraenoylamino]-(2,4-dihydroxy)phenylamide (5n in Scheme 1)

A mixture of all-trans retinoic acid (ATRA) (100 mg, 0.33 mmol) in dry DMF (1 mL) and dry CH$_2$Cl$_2$ (3 mL) was stirred under nitrogen atmosphere for 1 h. Oxalyl chloride (1.25 mmol, 108 μL) was added drop by drop at 0° C. The deep red reaction mixture was stirred for another 1.5 h at room temperature under nitrogen atmosphere. Very carefully removed the solvent, then added dry DMF (2 mL) for immediate use. At 0° C. under nitrogen atmosphere, Retinoyl chloride solution was added dropwise to a solution of 4-aminoresorcinol hydrochloride (0.666 mmol, 108 mg) and triethylamine (2.000 mmol, 2804) in dry DMF (1 mL). The dark-colored reaction mixture was stirred at room temperature and progress of the reaction was monitored using TLC. After the reaction completed 3 h, The reaction was quenched with saturated NH$_4$Cl (8 mL) and extracted with ethyl acetate (2×15 mL). The extracts were washed with (2×10 mL) and brine (2×10 mL), then dried overage Na$_2$SO$_4$, and evaporated. The residue was purified by flash column chromatography using hexane:ethyl acetate (5:1) as the eluent to give a yellow solid. 1H-NMR(300 MHz, CDCl$_3$): δ7.23 (d, 1H), 6.97 (d, 1H), 6.71~6.32 (m, 8H), 6.06 (s, 1H), 5.99 (s, 1H), 2.63 (s, 3H), 2.25 (br s, 5H), 1.92 (s, 3H), 1.57~1.44 (m, 4H), 1.24 (s, 6H). ESI MS:[M+H]$^+$408.13, calcd M 407.25 for C$_{26}$H$_{32}$NO$_3$.

(2E,4E,6E,8E)-[3,7-Dimethyl-9-(2,6,6-trimethyl-1-cyclohexenyl)-nona-2,4,6-tetraenoylamino]-(4-alcohol)phenylamide (5l in Scheme 1)

A mixture of all-trans retinoic acid (ATRA) (100 mg, 0.33 mmol) in dry DMF (2 mL) and dry CH$_2$Cl$_2$ (2 mL) was stirred under nitrogen atmosphere for 1 h. Oxalyl chloride (1.25 mmol, 108 μL) was added drop by drop at 0° C. The deep red reaction mixture was stirred for another 1.5 h at room temperature under nitrogen atmosphere. Very carefully removed the solvent, then added dry DMF (2 mL) for immediate use. At 0° C. under nitrogen atmosphere, Retinoyl chloride solution was added dropwise to a solution of 4-aminobezyl alcohol (0.66 mmol, 81.28 mg) and triethylamine (1.00 mmol, 140 μL) in dry DMF (2 mL). The dark-colored reaction mixture was stirred at room temperature until TLC analysis indicated none remaining (about 2~3 h). The reaction was quenched with saturated NH$_4$Cl and extracted with ethyl acetate. The extracts were washed with H$_2$O and brine, then dried overage Na$_2$SO$_4$, and evaporated. The residue was purified by flash column chromatography using hexane/ethyl acetate (4/1) as the eluent to give 5l as a yellow solid. 1H-NMR(300 MHz, CDCl$_3$): δ7.58 (d, 2H), 7.34 (d, 2H), 6.19 (m, 4H), 5.82 (s, 1H), 4.68 (s, 2H), 2.45 (s, 2H), 2.03 (br s, 5H), 1.74 (s, 3H), 1.67~1.62 (m, 2H), 1.51~1.49 (m, 2H), 1.05 (s, 6H). ESI MS:[M+H]$^+$406.20, calcd M 405.27 for C$_{27}$H$_{35}$NO$_2$.

(2E,4E,6E,8E)-[3,7-Dimethyl-9-(2,6,6-trimethyl-1-cyclohexenyl)-nona-2,4,6,8-tetraenoylamino]-(4-ethylalcohol)phenylamide (5 m in Scheme 1)

A mixture of all-trans retinoic acid (ATRA) (100 mg, 0.33 mmol) in dry DMF (2 mL) and dry CH$_2$Cl$_2$ (2 mL) was stirred under nitrogen atmosphere for 1 h. Oxalyl chloride (1.25 mmol, 108 μL) was added drop by drop at 0° C. The deep red reaction mixture was stirred for another 1.5 h at room temperature under nitrogen atmosphere. Very carefully removed the solvent, then added dry DMF (2 mL) for immediate use. At 0° C. under nitrogen atmosphere, Retinoyl chloride solution was added dropwise to a solution of 4-aminophenethyl alcohol (0.66 mmol, 90.5 mg) and triethylamine (1.00 mmol, 140 μL) in dry DMF (2 mL). The dark-colored reaction mixture was stirred at room temperature until TLC analysis indicated none remaining (about 2~3 h). The reaction was quenched with saturated NH$_4$Cl and extracted with ethyl acetate. The extracts were washed with H$_2$O and brine, then dried overage Na$_2$SO$_4$, and evaporated. The residue was purified by flash column chromatography using hexane/ethyl acetate (2/1) as the eluent to give 5m as a yellow solid. 1H-NMR(300 MHz, CDCl$_3$): δ8.03 (s, 1H), 7.52 (d, 2H), 7.20 (d, 2H), 6.32~6.18 (m, 4H), 5.82 (s, 1H), 3.85 (t, 2H), 2.98 (s, 2H), 2.90 (s, 1H), 2.85 (t, 2H), 2.44 (s, 2H), 1.91 (br s, 5H), 1.74 (s, 3H), 1.67~1.63 (m, 2H), 1.51~1.43 (m, 2H), 1.05 (s, 6H). ESI MS:[M+H]$^+$420.13, calcd M 419.28 for C$_{28}$H$_{37}$NO$_2$.

Peptidomimetic Derivatives of 4-HPR

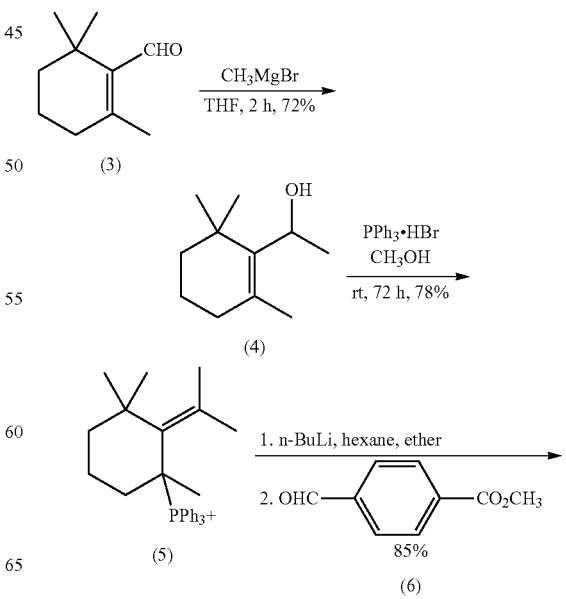

Scheme 2

Scheme 3

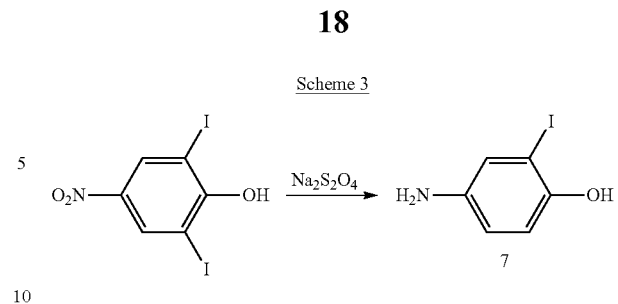

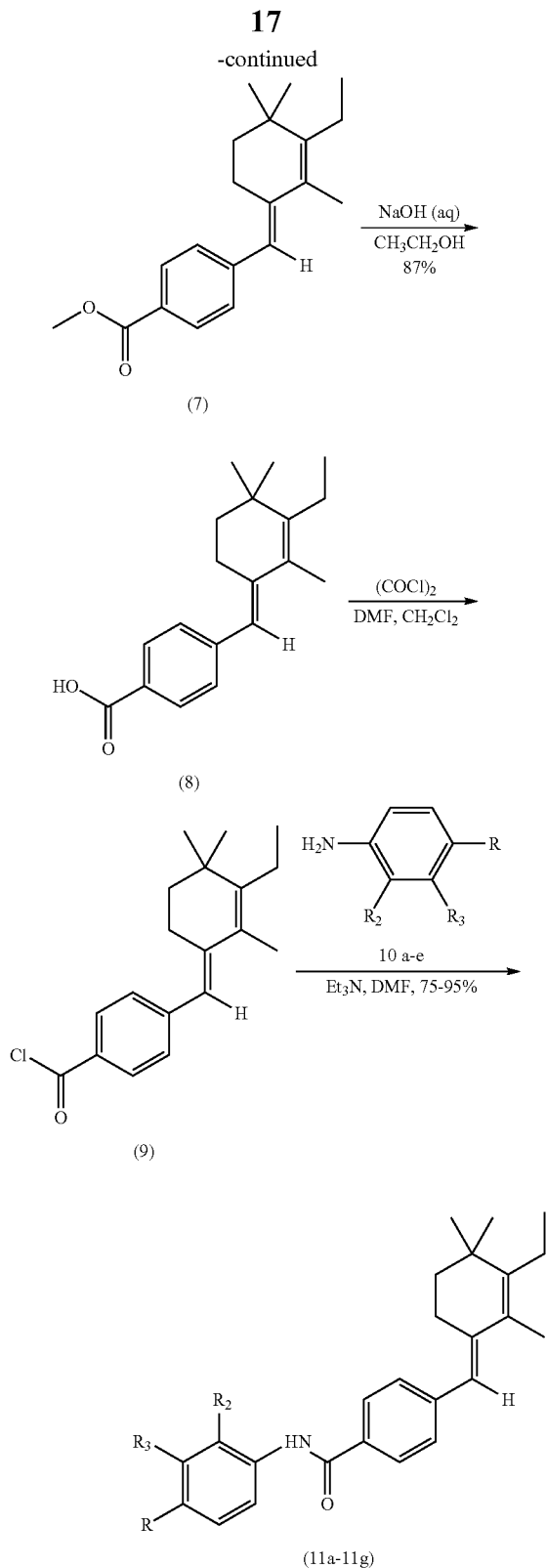

11a: R3 = R2 = H, R = OH
11b: R3 = Cl, R2 = H, R = OH
11c: R3 = F, R2 = H, R = OH
11d: R3 = I, R2 = H, R = OH
11e: R3 = H, R2 = OH, R = OH
11f: R3 = R2 = H, R = ―CH2OH
11g: R3 = R2 = H, R = ―CH2CH2OH

Experimental Procedures

Dry DMF was stored over 4-Å sieves and degassed before use by bubbling nitrogen through it for at least 1 h. The other reagents and solvents were purchased from commercially available sources and used without further purification. All reactions were conducted under a $N_2$ atmosphere. The reactions were monitored using TLC (Whatman® PE SIL G/UV Fluorescence $UV_{254}$). All the products prepared were purified by flash column chromatography on silica gel grade 62 (60-200 mesh, 150 Å). Proton nuclear magnetic resonance ($^1$H-NMR) were recorded in $CDCl_3$ using a Bruker 300 MHz instrument. Electrospray Ionization (ESI) mass spectra were determined on a. ThermoFinnigan LCQ Classic ion trap mass spectrometer (Waltham, Mass.) in positive ionization mode.

1-(2,6,6-Trimethyl-cyclohex-1-enyl)ethan-1-ol (4 in Scheme 2)

To a stirred solution of β-cyclocitral (2 g, 13.14 mmol) in dry tetrahydrofuran (40 mL) at 0° C. under nitrogen atmosphere, was added dropwise 3M methylmagnesium bromide in diethyl ether (5 mL). The reaction mixture was stirred for 30 min at 0° C. and for another 2 h at room temperature, then saturated aqueous $NH_4Cl$ was added and the heterogeneous mixture was stirred for 5 min. The organic layer was separated, and the aqueous phase was extracted with $Et_2O$ (25 mL×3). The combined organic extracts were washed with $H_2O$ (20 mL×2), brine (25 mL) and dried with $Na_2SO_4$. Removal of the solvent afforded 4 (2.15 g, 97%) as a yellow oil. $^1$H-NMR(300 MHz, $CDCl_3$): δ0.96 (s, 3H), 1.11 (s, 3H), 1.41~1.42 (m, 5H), 1.57~1.51 (m, 3H), 1.86 (s, 3H), 1.94~1.92 (m, 2H), 4.53~4.50 (dd, 1H).

(Compound 5 in Scheme 2).

To a suspension of triphenylphosphine hydrobromide (3.09 g, 9 mmol) in anhydrous methanol (25 mL) was added the prepared crude alcohol 4 (1.5 g, 8.91 mmol) in 5 mL anhydrous methanol and this suspension mixture was stirred at room temperature under $N_2$ atmosphere for 72 h. Methanol was removed from the resulting pale yellow solution and afforded solidified foam. After trituration with dry ether (50 mL), this foaming was changed into a powder by stirring for overnight. The resulting powder was filtered and washed with dry ether, and dried in air, to give a salt as a creamy white powder (4.23 g, 96%).

(Compound 7 in Scheme 2).

A solution of n-butyllithium in hexane (1.6M, 5.08 mL, 8.13 mmol) was added dropwise under $N_2$ atmosphere to a stirred suspension of the phosphonium salt 5 (4.013 g, 8.13 mmol) in dry ether (50 mL). The resulting dark red mixture was stirred at room temperature for 0.5 h. After the mixture was cooled to −78° C., a solution of methyl 4-formybenoate (1.335 g, 8.13 mmol) in dry THF (16 mL) was added dropwise over a period of 5 min, then, at −78° C., stirred 2-5 min. The reaction mixture became creamy light yellow and brown and was cloudy, slowly changed into reddish brown, and a large amount of off-white solid precipitated. After stirred at room temperature under $N_2$ atmosphere for 40 h, the mixture was filtered through a celite pad, and the resulting solid was washed with 120 mL of ether. The combined filtrates were concentrated to give a thick oil, which was purified by flash column chromatography eluant with Hexane/ethyl acetate (98/2) to give a brown oil (1.1 g). $^1$H-NMR (300 MHz, $CDCl_3$): δ8.01~7.98 (d, 2H), 7.36~7.32 (d, 2H), 6.47 (s, 1H), 3.93 (s, 3H), 2.62 (t, 2H), 2.25~2.23 (dd, 2H), 1.94 (s, 3H), 1.54~1.52 (t, 2H), 1.12~1.02 (m, 9H).

(Compound 8 in Scheme 2).

Ester 7 (1.077 g, 3.61 mmol) was dissolved in ethanol (17 mL), then was stirred under $N_2$ atmosphere for 0.5 h, added a solution of NaOH (0.833 g, 21 mmol in 36 mL $H_2O$). The reaction mixture was heated at reflux under $N_2$ atmosphere for 5 hr. The mixture became a clear yellow solution. After cooling slowly to a few degree above room temperature, the solution was acidified with concentrated HCl. A white solid was formed and was filted, washed with water and dried to give as white solid, which was recrystallized from hot ethanol and washed with dry hexane to give acid 8 as white crystals (0.85 g, 83%). $^1$H-NMR (300 MHz, DMSO): δ8.12.83 (bs, 1H), 7.90~7.87 (d, 2H), 7.41~7.38 (d, 2H), 6.47 (s, 1H), 2.56~2.54 (t, 2H), 2.21~2.18 (dd, 2H), 1.87 (s, 3H), 1.47~1.45 (t, 2H), 1.08~1.01 (m, 9H). ESI MS:$[M+H]^+$ 285.13, calcd M 284.18 for $C_{19}H_{24}O_2$.

(E)-4-((3-ethyl-2,4,4-trimethylcyclohex-2-enylidene) methyl)-N-(4-hydroxyphenyl)benzamide (Compound 11a in Scheme 2)

A mixture of acid 8 (200 mg, 0.703 mmol) in dry DMF (1 mL) and dry $CH_2Cl_2$ (8 mL) was stirred at room temperature under nitrogen atmosphere for 15 min. Oxalyl chloride (2.7 mmol, 230 μL) was added drop by drop at 0° C. The reaction mixture was stirred for another 1.5 h at room temperature under nitrogen atmosphere. The solvent was carefully removed, and dry DMF (2 mL) was added at 0° C. under nitrogen atmosphere. Then the acid chloride 9 solution was added dropwise to a solution of 4-aminophonol (1.41 mmol, 153 mg) and triethylamine (2.11 mmol, 300 μL) in dry DMF (2 mL). The reaction mixture was stirred at room temperature and progress of the reaction was monitored using TLC. After the reaction completed 3 h, the reaction was quenched with saturated $NH_4Cl$ (8 mL) and extracted with ethyl acetate (2×15 mL). The extracts were washed with (2×10 mL) and brine (2×10 mL), then dried overage $Na_2SO_4$, and evaporated. The residue was purified by flash column chromatography using hexane:ethyl acetate (2:1) as the eluent to give a white solid. $^1$H-NMR(300 MHz, DMSO): δ9.97 (s, 1H), 9.25 (s, 1H), 7.91~7.89 (d, 2H), 7.55~7.52 (d, 2H), 7.42~7.39 (d, 2H), 6.75~6.72 (d, 2H), 6.49 (s, 1H), 2.60~2.56 (t, 2H), 2.21~2.19 (dd, 2H), 1.87 (s, 1.88), 1.48~1.44 (t, 2H), 1.06~1.01 (m, 9H). ESI MS:$[M+H]^+$376.21, calcd M: 375.22 for $C_{25}H_{29}NO_2$.

(Compound 11b in Scheme 2).

A mixture of acid 8 (150 mg, 0.527 mmol) in dry DMF (1 mL) and dry $CH_2Cl_2$ (7 mL) was stirred at room temperature under nitrogen atmosphere for 15 min. Oxalyl chloride (1.95 mmol, 165 μL) was added drop by drop at 0° C. The reaction mixture was stirred for another 1.5 h at room temperature under nitrogen atmosphere. The solvent was carefully removed, and dry DMF (2 mL) was added at 0° C. under nitrogen atmosphere. Then the acid chloride 9 solution was added dropwise to a solution of 4-amino-2-chlorophenol (1.054 mmol, 151.3 mg) and triethylamine (2.11 mmol, 300 μL) in dry DMF (2 mL). The reaction mixture was stirred at room temperature and progress of the reaction was monitored using TLC. After the reaction completed 3 h, the reaction was quenched with saturated $NH_4Cl$ (8 mL) and extracted with ethyl acetate (2×15 mL). The extracts were washed with (2×10 mL) and brine (2×10 mL), then dried overage $Na_2SO_4$, and evaporated. The residue was purified by flash column chromatography using hexane:ethyl acetate (4:1) as the eluent to give a pale yellow solid (34.8 mg). $^1$H-NMR(300 MHz, DMSO): δ10.10 (s, 1H), 9.97 (s, 1H), 7.91~7.87 (dd, 2H), 7.84 (d, 2H),7.52~7.48 (dd, 1H), 7.43~7.40 (d, 2H), 6.96~6.93 (d, 1H), 6.49 (s, 1H), 2.60~2.59 (t, 2H), 2.21~2.19 (dd, 2H), 1.88 (s, 3H), 1.49~1.44 (t, 2H), 1.09~0.98 (m, 9H). ESI MS:$[M+H]^+$410.15, calcd M: 409.18 for $C_{25}H_{28}ClNO_2$.

(Compound 11c in Scheme 2).

A mixture of acid 8 (150 mg, 0.527 mmol) in dry DMF (1 mL) and dry $CH_2Cl_2$ (7 mL) was stirred at room temperature under nitrogen atmosphere for 15 min. Oxalyl chloride (1.95 mmol, 165 μL) was added drop by drop at 0° C. The reaction mixture was stirred for another 1.5 h at room temperature under nitrogen atmosphere. The solvent was carefully removed, and dry DMF (2 mL) was added at 0° C. under nitrogen atmosphere. Then the acid chloride 9 solution was added dropwise to a solution of 4-amino-2-fluorophenol (1.054 mmol, 134 mg) and triethylamine (2.11 mmol, 300 μL) in dry DMF (2 mL). The reaction mixture was stirred at room temperature and progress of the reaction was monitored using TLC. After the reaction completed 3 h, the reaction was quenched with saturated $NH_4Cl$ (8 mL) and extracted with ethyl acetate (2×15 mL). The extracts were washed with (2×10 mL) and brine (2×10 mL), then dried overage $Na_2SO_4$, and evaporated. The residue was purified by flash column chromatography using hexane:ethyl acetate (4:1) as the eluent to give a pale yellow solid (25.6 mg). $^1$H-NMR(300 MHz, DMSO): δ10.12 (s, 1H), 9.64 (s, 1H), 7.91~7.88 (d, 2H), 7.70 (d, 1H), 7.43~7.40 (d, 2H), 6.92 (t, 1H), 6.49 (s, 1H), 2.60~2.56 (t, 2H), 2.22~2.19 (dd, 2H), 1.88 (s, 3H), 1.48~1.44 (t, 2H), 1.07~1.01 (m, 9H). ESI MS:$[M+H]^+$ 394.17, calcd M: 393.21 for $C_{25}H_{28}FNO_2$.

4-amino-2-Iodophenol (Compound 7 in Scheme 3)

To a yellow suspension of 2,6-diiodo-4-nitrophenol (2.5 g, 6.44 mmol) in 50 mL of 25% NaOH, was added sodium dithionite (36 g) and the reaction mixture was heated and stirred at 75° C., until it was tuned white. After the reaction mixture was cooled to room temperature, 50 mL deionized water was added, and extracted with ethyl acetate (50 mL×5). The combined extracts were washed with water (30 mL×3), brine (30 mL) and dried with $Na_2SO_4$. Removed the solvent to give a brown oil, which was purified by flushing chromatography column, eluant with system A Hexane/ethyl acetate (6/1), then system B Hexane/ethyl acetate (3/1) to give a brown solid (0.27 g). $^1$H-NMR(300 MHz, DMSO): δ9.23 (s, 1H), 7.00~6.99 (d, 1H), 6.64~6.61 (d, 1H), 6.52~6.48 (d, 1H), 5.25 (bs, 2H).

(E)-4-((3-ethyl-2,4,4-trimethylcyclohex-2-enylidene) methyl)-N-(4-hydroxy-3-iodophenyl)benzamide (Compound 11d in Scheme 2)

A mixture of acid 8 (100 mg, 0.352 mmol) in dry DMF (1 mL) and dry $CH_2Cl_2$ (4 mL) was stirred at room temperature under nitrogen atmosphere for 15 min. Oxalyl chloride (1.31 mmol, 120 μL) was added drop by drop at 0° C. The reaction mixture was stirred for another 1.5 h at room temperature under nitrogen atmosphere. The solvent was carefully removed, and dry DMF (2 mL) was added at 0° C. under nitrogen atmosphere. Then the acid chloride solution (9) was added dropwise to obtain a solution of 4-amino-2-iodophenol (0.704 mmol, 165 mg) and triethylamine (2.11 mmol, 300 µL) in dry DMF (2 mL). The reaction mixture was stirred at room temperature and progress of the reaction was monitored using TLC. After the reaction was completed in 3 h, the reaction was quenched with saturated $NH_4Cl$ (8 mL) and extracted with ethyl acetate (2×15 mL). The extracts were washed with (2×10 mL) and brine (2×10 mL), then dried over $Na_2SO_4$, and evaporated. The residue was purified by flash column chromatography using hexane:ethyl acetate (4:1) as the eluent to give a pale yellow solid 151.36 mg (86%), mp: 170~171° C. $^1$H-NMR(300 MHz, DMSO): δ10.12 (s, 1H), 10.02 (s, 1H), 8.14 (d, J=2.3 Hz, 1H), 7.9 (d, J=8.3 Hz, 2H), 7.58 (dd, J=8.7 Hz, 2.3 Hz, 1H), 7.42 (d, J=8.3 Hz, 2H), 6.86 (d, J=8.7 Hz, 1H), 6.47 (s, 1H), 2.60 (m, 2H), 2.20 (q, J=7.5 Hz, 2H), 1.88 (s, 3H), 1.44 (m, 2H), 1.09 (s, 6H) and 1.04 (t, J=7.5 Hz, 3H). $^{13}$C NMR $CDCl_3$: δ 167.4, 149.1, 144.3, 144.2, 142.6, 142.5, 192.6, 129.6, 129.5, 129.5, 127.8, 127.4, 120.9, 120.9, 85.2, 61.1, 52.3, 39.2, 36.2, 28.03, 24.7, 23.3, 15.5, 15.1, and 14.7 ESI MS: calcd for $C_{25}H_{28}INO_2$ [M+H]$^+$) 502.12. found: 502.08.

(Compound 11e in Scheme 2).

A mixture of acid 8 (100 mg, 0.352 mmol) in dry DMF (1 mL) and dry $CH_2Cl_2$ (4 mL) was stirred at room temperature under nitrogen atmosphere for 15 min. Oxalyl chloride (1.31 mmol, 120 µL) was added drop by drop at 0° C. The reaction mixture was stirred for another 1.5 h at room temperature under nitrogen atmosphere. The solvent was carefully removed, and dry DMF (2 mL) was added at 0° C. under nitrogen atmosphere. Then the acid chloride 9 solution was added dropwise to a solution of 4-aminoresorcinol hydrochloride (0.704 mmol, 113.6 mg) and triethylamine (2.11 mmol, 300 µL) in dry DMF (2 mL). The reaction mixture was stirred at room temperature and progress of the reaction was monitored using TLC. After the reaction completed 3 h, the reaction was quenched with saturated $NH_4Cl$ (8 mL) and extracted with ethyl acetate (2×15 mL). The extracts were washed with (2×10 mL) and brine (2×10 mL), then dried overage $Na_2SO_4$, and evaporated. The residue was purified by flash column chromatography using hexane:ethyl acetate (5:1) as the eluent to give a white solid (44 mg). $^1$H-NMR(300 MHz, DMSO): δ9.52 (s, 1H), 9.42 (s, 1H), 9.23 (s, 1H), 7.93~7.90 (d, 2H), 7.42~7.39 (d, 2H), 7.29~7.26 (d, 1H), 6.49 (s, 1H), 6.37~6.36 (d, 1H), 6.26~6.24 (dd, 1H), 2.58~2.56 (t, 2H), 2.23~2.19 (dd, 2H), 1.88 (s, 3H), 1.48~1.44 (t, 2H), 1.07~1.01 (m, 9H). ESI MS:[M+H]$^+$392.15, calcd M: 391.21 for $C_{25}H_{29}NO_3$.

Example II

Biological Studies

Part 1. Effects of Fenretinamide Derivatives on Tumor Cell Growth
Introduction

Rhabdoid tumors (RTs) are highly aggressive and mostly incurable pediatric malignancies that arise in brain, kidneys and soft tissues (27, 84). RTs most commonly occur in children younger than five years of age with a peak incidence between birth and three years of age (27). Irrespective of their location, all RTs are characterized by the presence of sheets or nests of rhabdoid cells and exhibit biallelic deletions and/or mutations in the INI1/hSNF5 gene, located at chromosome 22q11.2 (85-88). Current therapeutic regimens for RTs involve empirically selected combinations of chemotherapeutic agents that are highly toxic and rarely curative, and hence the survival rate for children with RTs remains poor (27, 84, 89-91). Thus, there is a dire need to develop novel therapeutic strategies for RTs, preferably based on the understanding of molecular factors responsible for the genesis, growth and survival of these tumors. Cyclin D1 is essential for the genesis and survival of RTs, and chemotherapeutic agents such as 4-HPR, which target Cyclin D1, are effective in inhibiting the growth of RTs in preclinical models (28, 29).

Materials and Methods

Cell Culture and Materials.

The rhabdoid cell line (MON) (88) was cultured in RPMI 1640 supplemented with 10% fetal bovine serum, 2 mM L-glutamine, 50 U/ml penicillin, and 50 µg/ml streptomycin at 37° C. with 5% $CO_2$ and 95% humidified air. 4-(Fenretinide) was either obtained from NCI or synthesized in house. Fenretinide or its synthetic derivatives were reconstituted in 100% ethanol as a 10 mM solution and the aliquots were stored frozen at −80° C., protected from light. Working solutions (50 µM or 200 µM) and serial dilutions were prepared by diluting the stock solution with culture medium, such that the concentration of ethanol was <2% in all dilutions.

MTS Assays to Test the Activity of Fenretinide and its Derivatives in Inhibiting the Survival of Rhabdoid Tumor Growth.

Aliquots of $8\times10^3$ MON cells were plated in 96-well microdilution plates. Twenty four hours after seeding, the cells were treated with serial dilutions of each drug. Following incubation for 24 or more hours, each well was stained with 20 µl of MTS [3-(4,5-dimethylthiazol-2-yl)-5-(3-carboxymethoxyphenyl)-2-(4-sulfophenyl)-2H-tetrazolium, inner salt] that was mixed 20:1 V/V in PMS (phenazine methosulphate, CellTiter 96® AQueous Non-Radioactive Cell Proliferation Assay Kit, Promega, Madison, Wis.) added to each of the well in the microtiter plate containing 100 µl of culture medium. After 4 h incubation, the plates were analyzed by an ELISA plate reader (Wallac Victor, 1420 Multilabel Counter, Perkin Elmer) at 490 nm wave-length. Cell plating, drug treatment and survival assay were performed using the epMotion 5070 automated liquid handling robotic system (Eppendorff, Westbury, N.Y.).

Statistical Analysis and Determination of IC50 Values.

Statistical analysis of the data was carried out using Graph-Pad Prism (San Diego, Calif.). Relative IC50 values were calculated using the nonlinear regression curve fit with sigmoidal dose response (variable slope) function. Relative IC50 is defined as the concentration giving a response exactly half way between the fitted top and bottom of the survival curve when graphed as percent inhibition versus the log of the concentration of compound. The fitting error, or standard error describes the error involved in fitting the curve.

Immunoblot Analysis.

This assay was performed using a routine laboratory protocol as previously described using chemiluminescence detection method (30). The following antibodies were used: polyclonal α-cyclin D1 Ab-3 (NeoMarkers, Cat# RB-010-P0), monoclonal α-cyclin D1 DCS-6 (NeoMarkers, Cat# MS-210-P1), α-β-Actin (Sigma Cat# A5441) and α-Tubulin-α (Sigma, Cat # T5168).

Results

Fenretinamide Derivatives with Phenyl Group Substitutions

Survival assay was carried out testing the effect of a first set of compounds (5a-5d) and comparing their effect on MON cells to that of the parent compounds 4-HPR and retinoic acid (ATRA). The structures of compounds 5(a)-5(n) (from Scheme 1) are shown in Table 1.

TABLE 1
Structure and IC50 of compounds tested.
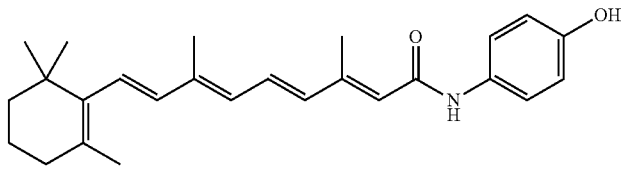
FL-A- 74
IC 50 = 19 μM
5(g)
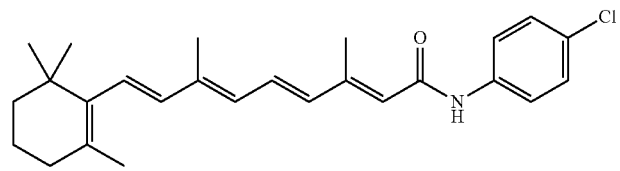
FL-A- 64
IC 50 = >200 μM
5(b)
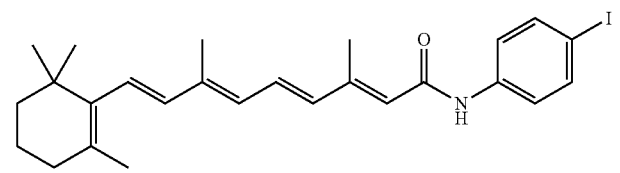
FL-A- 22
IC 50 = n/a precipitated
5(d)
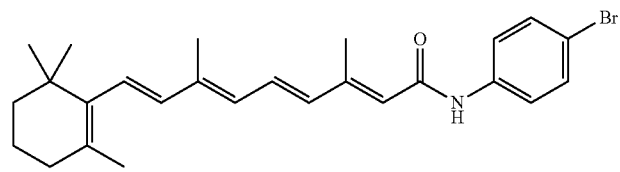
FL-A- 73
IC 50 = 150 μM
5(c)
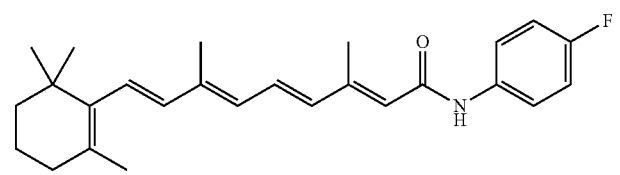
FL-A- 16
IC 50 = 150 μM
5(a)
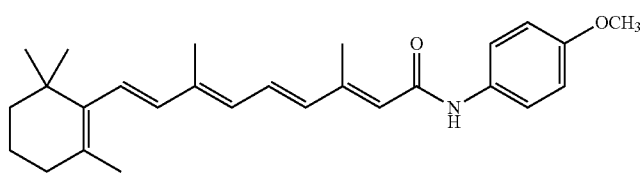
FL-A- 87
IC 50 = n/a precipitated
5(f)

TABLE 1-continued
Structure and IC50 of compounds tested.
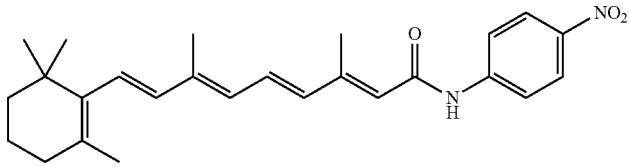
FL-A- 89
IC50 = >200 μM
5(e)
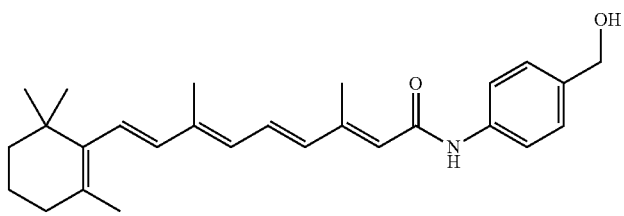
FL-A- 240
IC 50 = 25 μM
5(l)
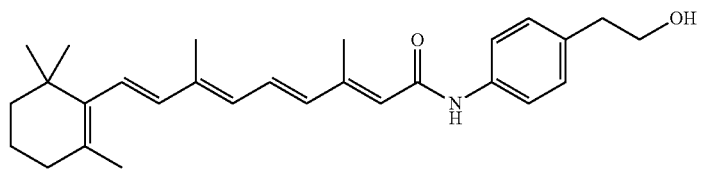
FL-A- 252
IC 50 = >50 μM
5(m)
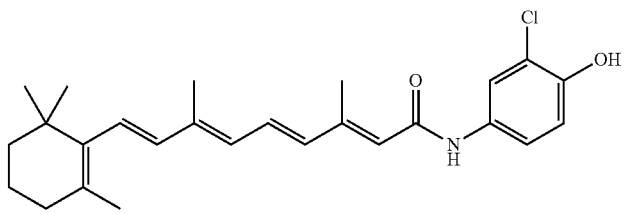
FL-A- 59
IC 50 = 10 μM
5(i)
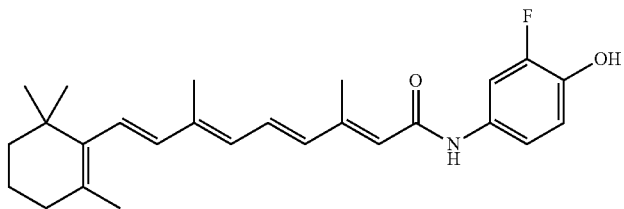
FL-A- 111
IC 50 = 8 μM
5(h)

TABLE 1-continued

Structure and IC50 of compounds tested.

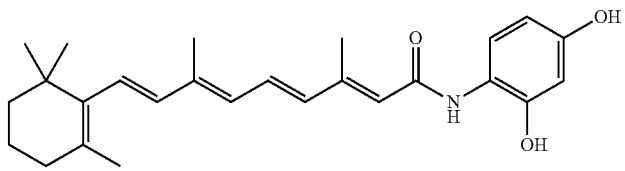

FL-A-102
IC 50 = 8 μM
5(n)

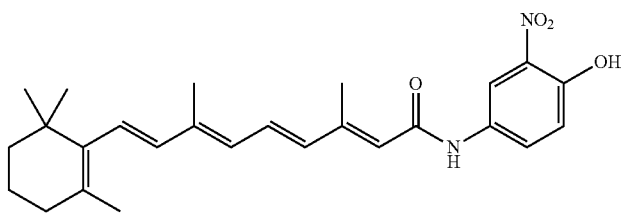

FL-A-107
IC 50 = n/a precipitated
5(k)

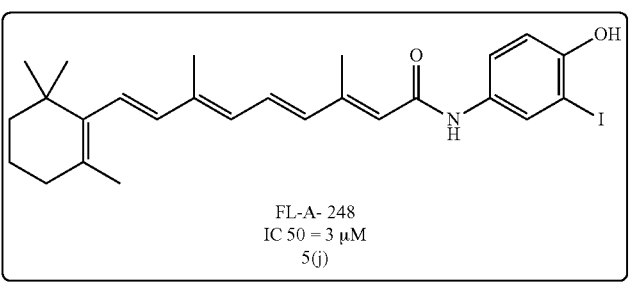 [SMILES: CC1=C(/C=C/C(C)=C/C=C/C(C)=C/C(=O)Nc2ccc(O)c(I)c2)C(C)(C)CCC1]

FL-A-248
IC 50 = 3 μM
5(j)

The results of survival assay indicated that while 4-HPR exhibited an IC50 of ~15 μM, Retinoic acid (IC50 100 μM), was largely ineffective in inhibiting the growth of rhabdoid cells (FIG. 1A). Substitution at the para position with any of the halogens, i.e. chloro-[5(b)], iodo-[5(d)], fluoro-[5(a)], or bromo-[5(c)] moieties, greatly reduced the activity of 4-HPR in RT cells (IC50s increased to 150 μM or greater, FIG. 1A), though 5(d) precipitated in cell culture medium and therefore IC50 was not determined (FIG. 1A).

To determine if the reduction in the activity in 4-HPR compounds was due to the presence of halogen groups or other reasons, the para-hydroxy group was substituted with alternatives including the methoxy [5(f)], and nitro [5(e)] moieties. The para-methoxy derivative was insoluble in cell culture medium and the para-nitro derivative [5(e)] was largely ineffective, with an IC50 greater than 200 μM (FIG. 1B).

Figure 1C:
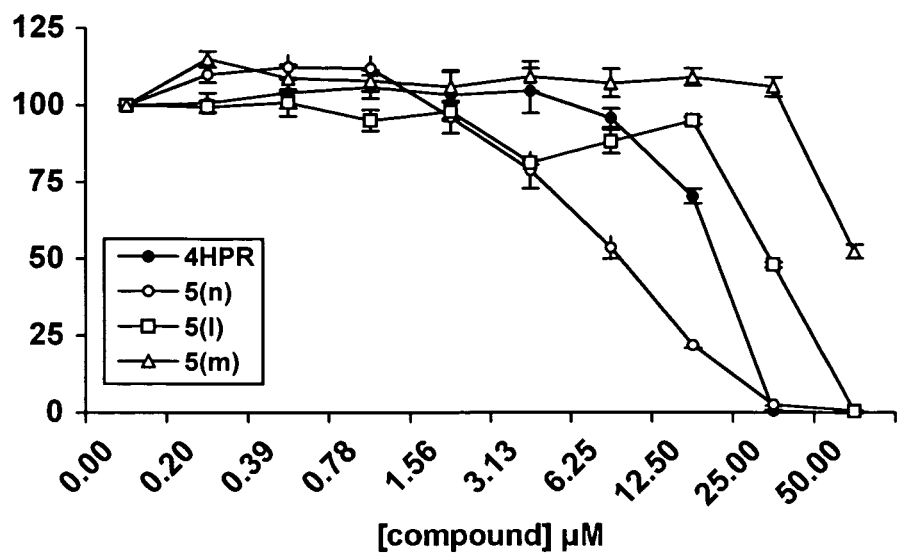
Figure 1D:
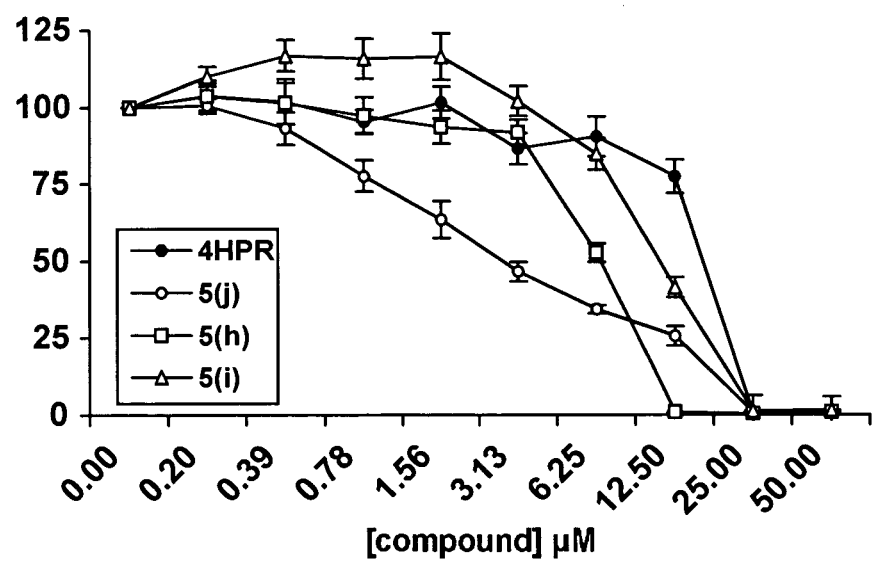

2,4 dihydroxy, or 4-methyl and 4-ethyl hydroxy phenyl derivatives were synthesized to determine if a fixed position is required for the hydroxyl group on the phenyl ring or extending the carbon chain is tolerated. Substitution of methyl [5(1)] or ethyl hydroxy [5(m)] derivatives at para position resulted in lack of activity consistent with the idea that a fixed position for the para-hydroxy group is important for activity (FIG. 1C). Interestingly, 2,4-hydroxy derivative [5(n)], has more activity compared to 4-HPR (IC50 8 μM, FIG. 1C). These results suggested that substitutions at meta-position of phenyl group can enhance the activity.

The above results indicated that the hydroxy group at the para-position is important for 4-HPR activity in RT cells. Furthermore, 2,4-dihydroxy derivatives were more active indicating that addition at meta-position is tolerated. To further confirm these observations and to derive halogen substituted compounds of 4HPR, the next set of derivatives was synthesized with substitutions at the meta positions, keeping the 4-OH group intact. Addition of fluoro-[5(h)] and chloro-[5(i)] halogen moieties to the meta-position resulted in compounds with similar or slightly more activity compared to 4-HPR in RT cells (IC50 of 8 μM and 10 μM respectively, FIG. 1D). Substitution of a nitro group at meta-position [5(k)], resulted in a compound that was insoluble in cell culture medium. Interestingly, substitution of iodo-moiety at meta position [5(j)] substantially increased the efficacy (IC50~3 μM, FIG. 1D). These results indicate that the presence of the para-hydroxy group is important for maintaining the efficacy of 4-HPR and its derivatives against rhabdoid tumors, and that the substitution at meta position is tolerated. The IC50 values for the compounds in FIG. 1A-1D are shown in Table 2.

TABLE 2

IC50 values for compounds in FIG. 1A-1D.

| FIG. | Compound | IC50 in μM |
|---|---|---|
| 1A | 4HPR | 9 |
| | ATRA | 100 |
| | 5(g) | 19 |
| | 5(c) | 150 |
| | 5(b) | >200 |

TABLE 2-continued

IC50 values for compounds in FIG. 1A-1D.

| FIG. | Compound | IC50 in μM |
|---|---|---|
|  | 5(a) | 150 |
|  | 5(d) | n/a |
| 1B | 4HPR | 12 |
|  | 5(f) | n/a |
|  | 5(e) | >200 |
| 1C | 5(l) | 25 |
|  | 5(m) | >50 |
|  | 5(n) | 8 |

TABLE 2-continued

IC50 values for compounds in FIG. 1A-1D.

| FIG. | Compound | IC50 in μM |
|---|---|---|
| 1D | 4HPR | 19 |
|  | 5(h) | 8 |
|  | 5(k) | n/a |
|  | 5(j) | 3 |
|  | 5(i) | 12.5 |

$IC_{50}$ concentration = the concentration of drug required to kill 50% of cells.

Other results obtained with the analysis of biological activity of Fenretinide derivatives are summarized in Table 3.

TABLE 3

Structure, cytotoxic activities and effect on biomarker expression of Fenretinide derivatives.

| Compound | Structure | IC50 (in regular FBS) μM | IC50 (in charcoal adsorbed serum) μM | Repression of Cyclin D1 |
|---|---|---|---|---|
| Retinoic acid (ATRA) | 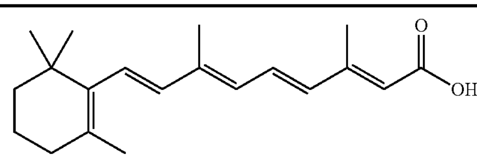 | >50 | >15 | No |
| Fenretinide (4-HPR) | 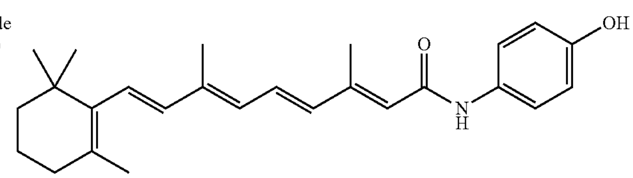 | 12-19 | 2 | Yes |
| FLA(A)16 5(a) | 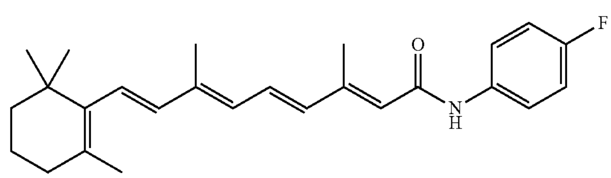 [SMILES: CC1=C(/C=C/C(C)=C/C=C/C(C)=C/C(=O)Nc2ccc(F)cc2)C(C)(C)CCC1] | >50 | >15 | No |
| FLA(A)22 5(d) | 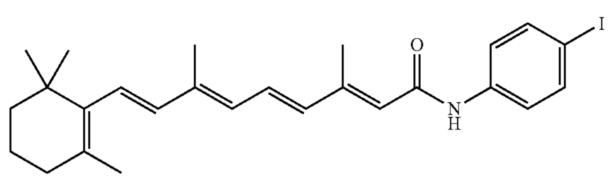 [SMILES: CC1=C(/C=C/C(C)=C/C=C/C(C)=C/C(=O)Nc2ccc(I)cc2)C(C)(C)CCC1] | >50 | >15 | No |
| FLA(A)59 5(i) | 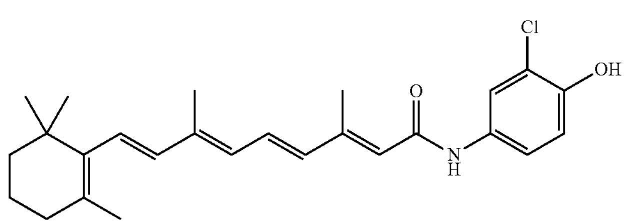 | 10 | 1.5 | Yes |
| FL(A)102 5(n) | 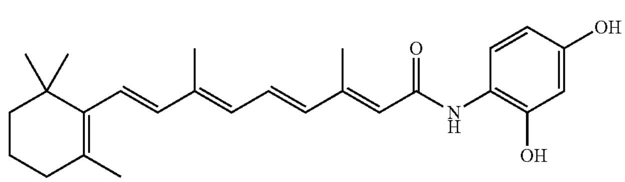 [SMILES: CC1=C(/C=C/C(C)=C/C=C/C(C)=C/C(=O)Nc2ccc(O)cc2O)C(C)(C)CCC1] | 8 |  | Yes |

TABLE 3-continued

Structure, cytotoxic activities and effect on biomarker expression of Fenretinide derivatives.

| Compound | Structure | IC50 (in regular FBS) µM | IC50 (in charcoal adsorbed serum) µM | Repression of Cyclin D1 |
|---|---|---|---|---|
| FL(A)111 5(h) | 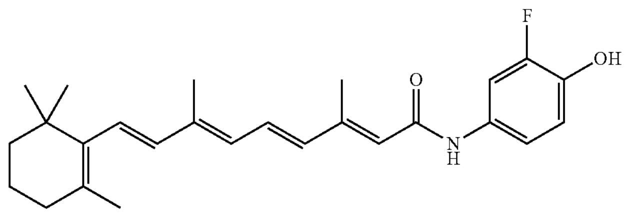 [SMILES: CC1=C(/C=C/C(C)=C/C=C/C(C)=C/C(=O)Nc2ccc(O)c(F)c2)C(C)(C)CCC1] | 8 | | Yes |
| FL(A)248 5(j) | 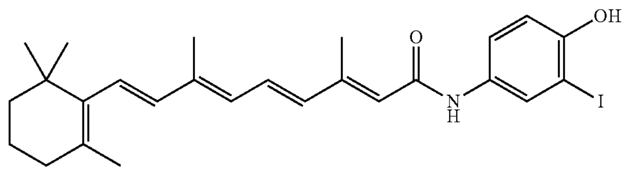 [SMILES: CC1=C(/C=C/C(C)=C/C=C/C(C)=C/C(=O)Nc2ccc(O)c(I)c2)C(C)(C)CCC1] | 3 | 0.8 | Yes |

Peptidomimetic Derivatives of 4-HPR

Figure 2:
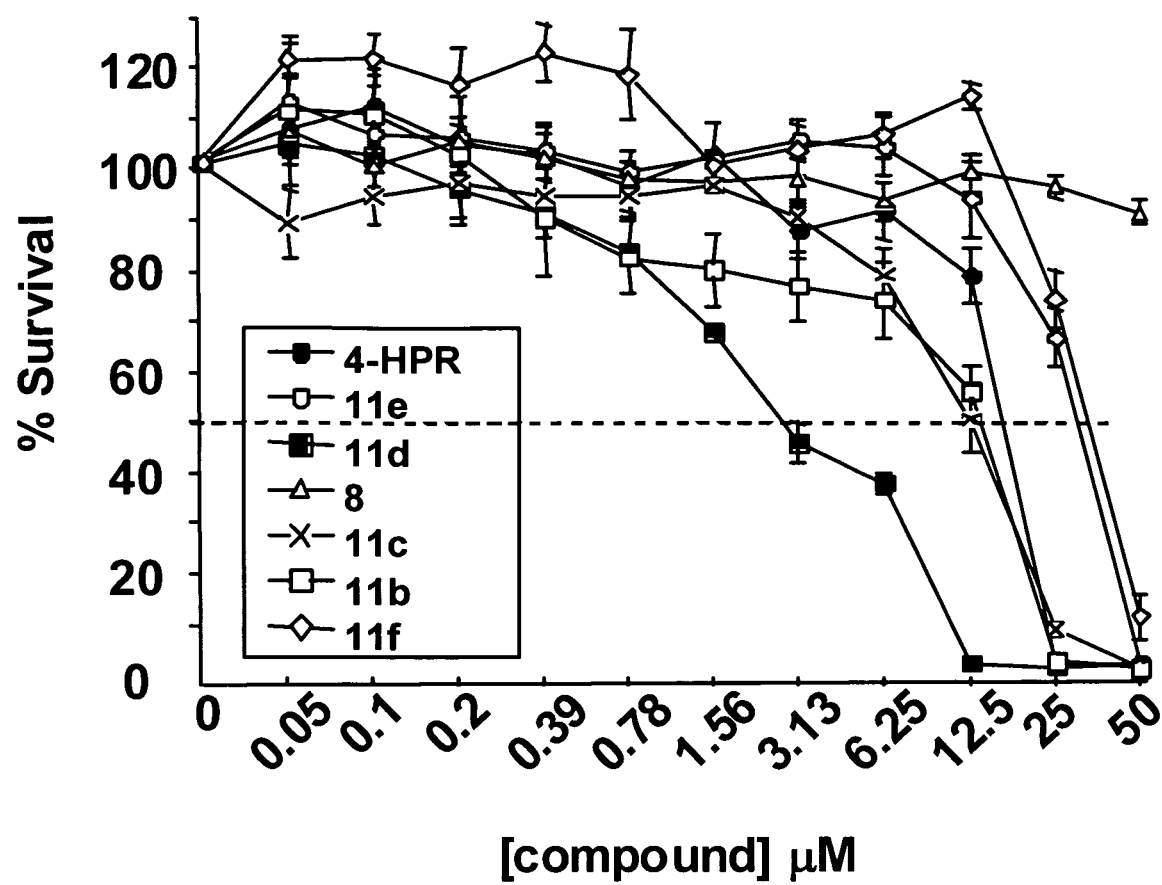
FIG. 2. Effect of fenretinide peptidomimitic derivatives on the survival of rhabdoid tumor cells in culture. % survival of MON rhabdoid tumor cells treated with fenretinide derivatives, when compared to the vehicle treated control. The data in all the panels represent the average of triplicate experiments, and the standard error is indicated.

Several compounds were synthesized by substituting the alkene backbone with a ring structure and in addition further modifying the 4OH-phenyl moiety. Compound (11a) and its derivatives (11b-11g), were obtained as represented in Scheme 2. These compounds were tested in a biological survival assay (FIG. 2, Table 4).

The peptidomimetic compound 11a exhibited similar cytotoxicity profile as compared to 4-HPR at lower concentrations of the drugs tested. However, the compounds 11a and 11g precipitated in cell culture medium and therefore, the exact IC50 value for these compounds could not be determined. Compounds 11 e, 11 f, and 8, exhibited IC50 values of 47.18 µM, 29.06 µM, and >50 µM respectively, which are much greater than the parent compounds. Two compounds with chloro- and flouro-substitutions at the meta-position of the phenyl group (compounds 11b and 11c respectively), exhibited similar level of activities to that of the parent 4-HPR compound (IC50 values of 10-13 µM, respectively). Interestingly, compound 11d, with substitution of an iodo-moiety at the meta-position of the phenyl ring demonstrated improved efficacy with IC50 reduced to 3 µM. This compound did not show any precipitation in the culture conditions.

Part 2. Activities of Halogen Substitutes and Peptidomemitic Derivatives of Fenretinide are Correlated to Down-Modulation of Cyclin D1 in Rhabdoid Tumor Cells Rhabdoid tumors arise due to loss of INI1 tumor suppressor. INI1 directly represses Cyclin D1 and rhabdoid tumors are exquisitely dependent on Cyclin D1 for genesis, indicating that targeting the Cyclin/cdk axis is an effective novel strategy against these tumors. Since, rhabdoid tumors are exquisitely sensitive to Cyclin D1, the ability of fenretinide derivatives to down-modulate Cyclin D1 was determined.

The effects of fenretinide, halogen substitutes, and peptidomimetic derivatives on cell cycle regulation and apoptosis were tested by using: i) cell survival assay (MTS); ii) FACS analysis; and iii) immunoblot analysis to determine the effect on Cyclin D1.

Figure 3A:
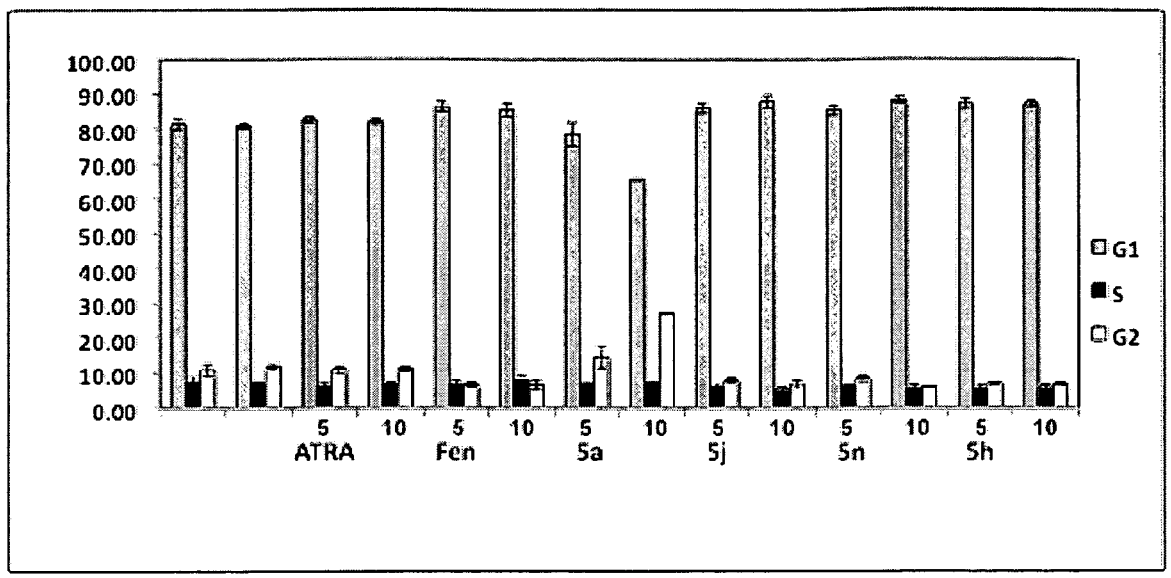
FIG. 3A-3B. Induction of cell cycle arrest and apoptosis by halogen derivatives of fenretinide. A. Cell cycle profile determined by FACS analysis of MON cells treated with either 5 or 10 μM concentrations of fenretinide and its derivatives for 2 days. Percentage of cells at various stages of cell cycle (G1, S and G2) is indicated. B. Percentage of MON cells at sub-$G_1$ when exposed for 2 days to fenretinide and its derivatives.
Figure 3B:
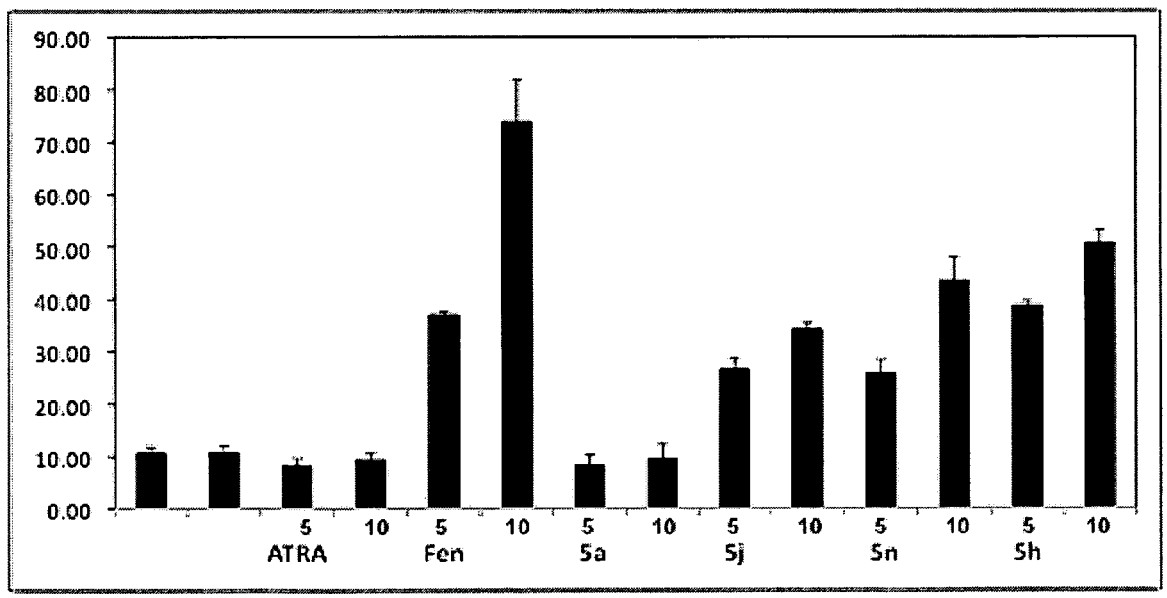
Figure 4A:
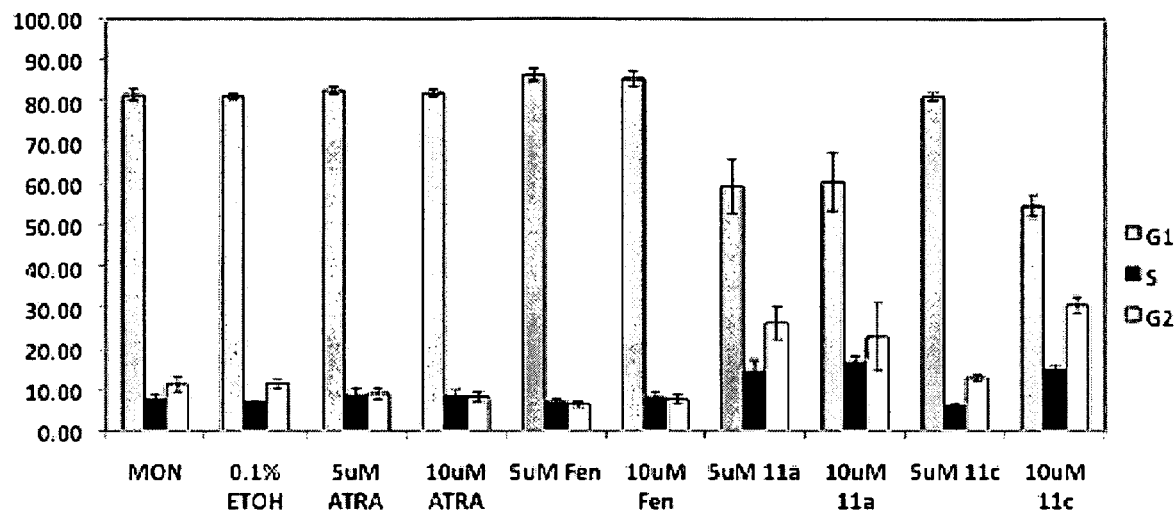
FIG. 4A-4B. Induction of cell cycle arrest and apoptosis by peptidomimetic derivatives of fenretinide. A. Cell cycle profile determined by FACS analysis of MON cells treated with either 5 or 10 μM concentrations of fenretinide and its derivatives for 2 days. Percentage of cells at various stages of cell cycle (G1, S and G2) is indicated. B. Percentage of MON cells at sub-$G_1$ when exposed for 2 days to fenretinide and its derivatives.
Figure 4B:
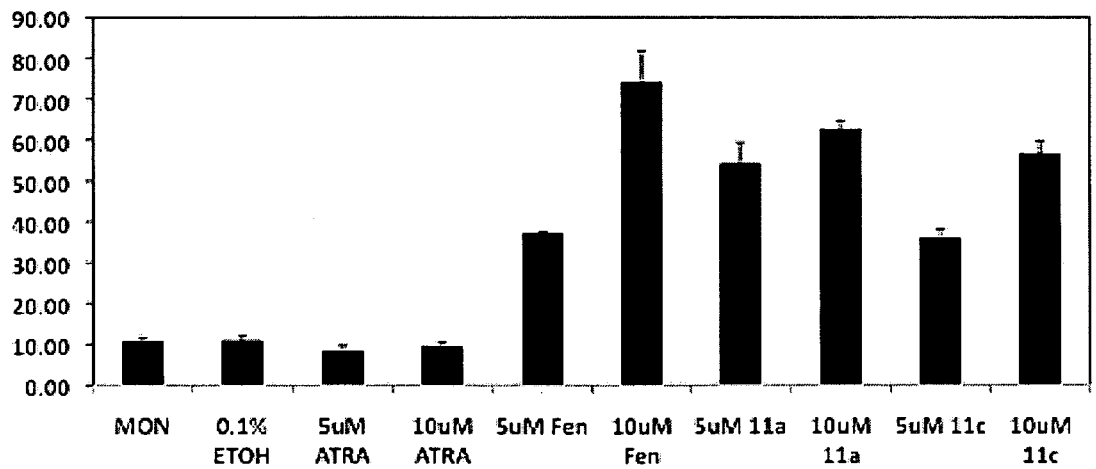
Figures 5A, 5B:
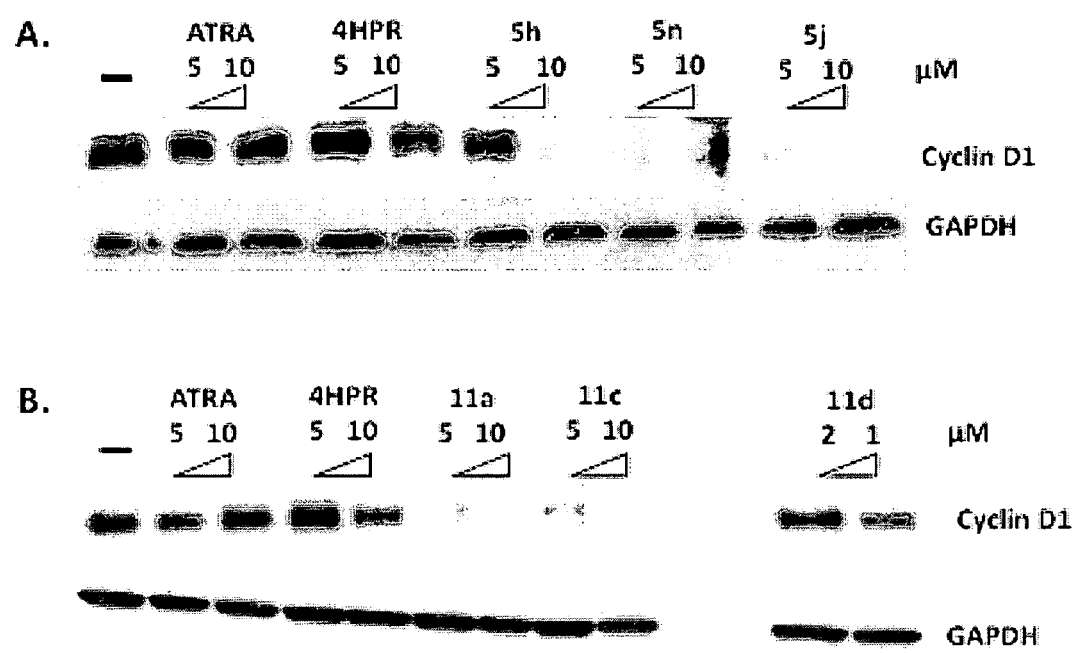
FIG. 5A-5B. Effect of fenretinide, its derivatives and peptidomimetic compounds on expression of Cyclin D1. Immunoblot analysis to determine the effect of fenretinide and its halogen substitutes (A) and peptidomimetic compounds (B). GAPDH is a loading control.

Exposure of rhabdoid tumor cells to active derivatives and peptidomimetics inhibited their survival. The active compounds (but not inactive compounds and all-trans retinoic acid (ATRA)) were able to induce G1 arrest and apoptosis; and down modulate Cyclin D1. These compounds were also active against other tumor cells. FIGS. 3 and 4 indicate the induction of cell cycle arrest and apoptosis by the different compounds. Tables 5 and 6 show data illustrating the effects on cell cycle and apoptosis induction when MON cells were exposed to different compounds. FIG. 5 shows the effect of fenretinide, its derivatives and peptidomimetic compounds on expression of Cyclin D1.

TABLE 4

IC50 values for compounds.

| Compound | Relative IC50 in µM | Fitting Error (+/−SEM) |
|---|---|---|
| 4-HPR | 14.68 | .221 |
| 8 | >50 | NA[a] |
| 11(b) | 10.44 | .227 |
| 11(c) | 12.88 | .077 |
| 11(d) | 3.149 | .190 |
| 11(e) | 47.18 | .652 |
| 11(f) | 29.06 | .083 |

[a]IC50 greater than the highest concentration tested.

TABLE 5

Data illustrating the effect on cell cycle and apoptosis induction when MON cells were exposed for 2 days to halogen derivative of Fenretinide. A. Percentage of cells at various stages of cell cycle (G1, S and G2) is indicated. B. Percentage of MON cells at sub-$G_1$

| | | A. | | | | B. | |
|---|---|---|---|---|---|---|---|
| Drug | µM | % G1 | % S | % G2 | Drug | µM | SubG1 |
| | 0 | 81.52 | 7.56 | 10.92 | | 0 | 10.64 |
| | 0 | 81.08 | 6.98 | 11.93 | | 0 | 10.80 |
| ATRA | 5 | 82.64 | 6.32 | 11.04 | ATRA | 5 | 8.22 |
| | 10 | 82.08 | 6.71 | 11.21 | | 10 | 9.27 |

TABLE 5-continued

Data illustrating the effect on cell cycle and apoptosis induction when MON cells were exposed for 2 days to halogen derivative of Fenretinide. A. Percentage of cells at various stages of cell cycle (G1, S and G2) is indicated. B. Percentage of MON cells at sub-$G_1$

| | A. | | | | B. | |
|---|---|---|---|---|---|---|
| Drug | μM | % G1 | % S | % G2 | Drug | μM | SubG1 |
| Fen | 5 | 86.32 | 6.95 | 6.73 | Fen | 5 | 37.12 |
| | 10 | 85.41 | 7.93 | 6.66 | | 10 | 73.98 |
| 5a | 5 | 78.56 | 6.84 | 14.61 | 5a | 5 | 8.30 |
| | 10 | 65.50 | 7.25 | 27.25 | | 10 | 9.44 |
| 5j | 5 | 86.11 | 6.06 | 7.83 | 5j | 5 | 26.48 |
| | 10 | 87.97 | 5.16 | 6.87 | | 10 | 34.21 |
| 5n | 5 | 85.42 | 6.11 | 8.48 | 5n | 5 | 25.81 |
| | 10 | 88.30 | 5.65 | 6.05 | | 10 | 43.53 |
| 5h | 5 | 87.23 | 5.67 | 7.10 | 5h | 5 | 38.78 |
| | 10 | 87.22 | 5.81 | 6.97 | | 10 | 50.79 |

TABLE 6

Data illustrating the effect on cell cycle and apoptosis induction when MON cells were exposed for 2 days to peptidomimetic derivative of Fenretinide. A. Percentage of cells at various stages of cell cycle (G1, S and G2) is indicated. B. Percentage of MON cells at sub-$G_1$

| | A. | | | | B. | |
|---|---|---|---|---|---|---|
| Drug | μM | % G1 | % S | % G2 | Drug | μM | SubG1 |
| | 0 | 81.52 | 7.56 | 11.31 | | 0 | 10.64 |
| | 0 | 81.08 | 6.98 | 11.48 | | 0 | 10.80 |
| | 5 | 82.64 | 8.58 | 9.07 | | 5 | 8.22 |
| ATRA | 10 | 82.08 | 8.51 | 8.18 | ATRA | 10 | 9.27 |
| | 5 | 86.32 | 6.95 | 6.49 | | 5 | 37.12 |
| Fen | 10 | 85.41 | 8.02 | 7.60 | Fen | 10 | 73.98 |
| | 5 | 59.33 | 14.49 | 26.19 | | 5 | 53.97 |
| 11a | 10 | 60.40 | 16.76 | 22.84 | 11a | 10 | 62.59 |
| | 5 | 81.11 | 5.98 | 12.92 | | 5 | 35.76 |
| 11c | 10 | 54.64 | 14.83 | 30.52 | 11c | 10 | 56.62 |

Example III

Synthesis of Nanoparticles Conjugates of 4-HPR

In this study, monocrystalline magnetic nanoparticles will be used, with core of (Fe2O3)n (Fe3O4)m covered with a layer of 10-20 kDa dextran. Cross linking with epichlohydrin and amination with ammonia will provide free amine groups for attachment of biomolecules (4-HPR) derivatives or radio-labeled (4-HPR) derivatives. The final products will be purified with GPC (sephadex G columns). $^{18}$F radiotracers and $^{124}$I radiotracers will be used. In general, two types of radio-labeled compounds can be prepared, one type containing only radiotracers and other type radiotracers conjugated with nanoparticles. Radiolabeled compounds can be used for therapeutic and/or imaging purposes.

Scheme 4.
Schematic diagram to synthesize nanoparticle conjugated biomolecules

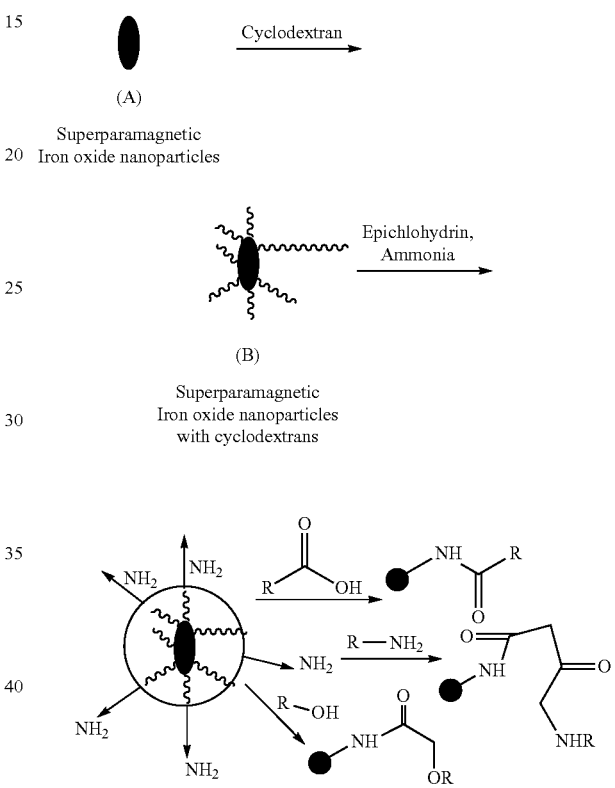

(Conjugation Strategies: Aminated Magnetofluorescent nanoparticles

Scheme 5.
Conjugation of 4-HPR derivatives with nanoparticles

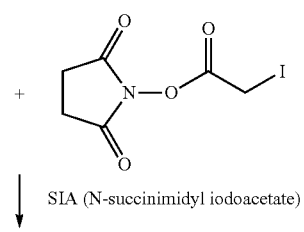

SIA (N-succinimidyl iodoacetate)

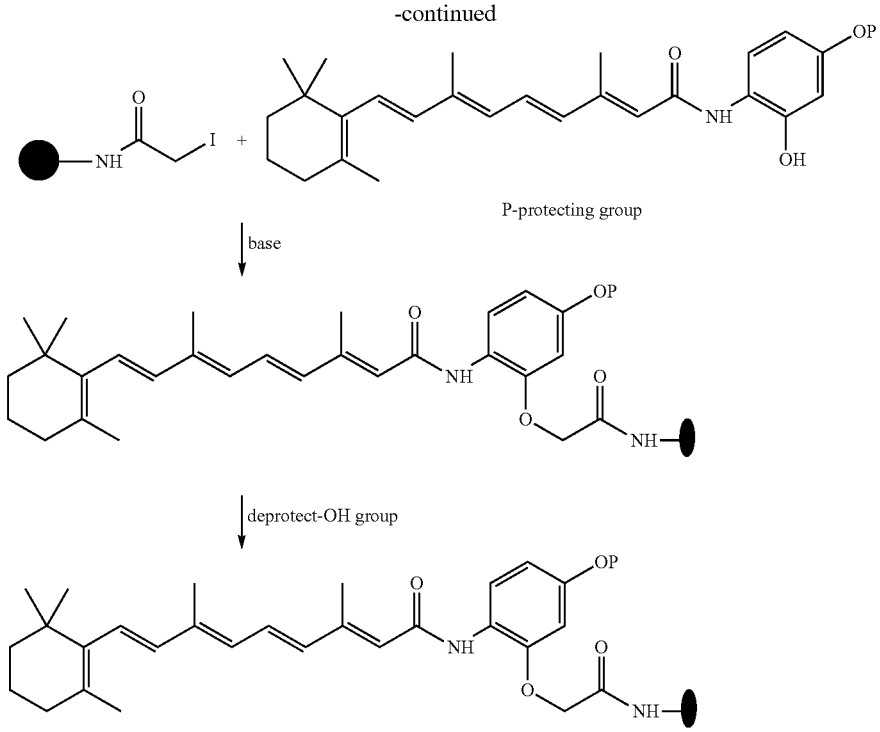

Conjugation of 4-HPR Derivatives with Nanoparticles.

While many 4-HPR derivatives can be used as starting material for conjugating to nanoparticle, the observation that dihydroxyphenyl retinamide [compound FL(A)102] retains 4-HPR activity provides an immediate method for developing nanoparticle conjugates that are likely to retain their activity. The following is a general procedure and a scheme for nanoparticle conjugates of 4-HPR.

General Procedure:

A solution of succinimidyl iodoacetae (SIA) and DMSO (Dimethyl Sulfoxide) will be stirred for 1 hr; then to the resulting solution nanoparticles will be added. The solution will be protected from light and well shaken. After completion of the reaction, the excess SIA will be removed from suspension through gel filtration chromatography. The hydroxylated Nanoparticle conjugate will be purified by a Sephadex G-25 column eluted with PBS buffer (69). The amine and carboxyl derivatives of 4-HPR will be conjugated using the procedure described by Ralph and co-workers (77).

Discussion

4-HPR is a synthetic retinamide that has promising anticancer activity and minimal toxicity in humans. To obtain derivatives of 4-HPR that lend themselves to further modifications such as conjugation with nano-particles or radiochemicals, the active moeity of 4-HPR required for its cytotoxic activity on rhabdoid cells was identified. As disclosed herein, substitution of para-hydroxy group with halogens, nitro, methoxy, hydroxmethyl or hydroxyethyl groups abolished cytotoxic activity. However, ortho- and meta-positions can be substituted, for example, with halogens or hydroxy groups. Substitution of halogens at the meta-position retained the cytotoxic activity, with iodo-substitutions exhibiting better IC50 values than parent 4-HPR.

The present study demonstrated that the 4-hydroxy position of 4-HPR is important for its activity. This conclusion was not made in a previous study which indicated that side chain length of the functional group may correlate with activity (92). The present studies indicate that the 4-hydroxy group may directly contact the target protein in the RT cells to mediate its activity. It has been demonstrated that 4-HPR binds to RAR-13 and RAR-γ more tightly when compared to that of all trans retinoic acid (ATRA) but activates these receptors to a lesser extent. Furthermore, studies of 4-HPR derivatives indicate that the cytotoxic activity is not correlated to RAR activation (92). Consistent with this idea, ATRA did not have appreciable cytotoxic activity in the present cell culture models.

The iodo-derivative compounds 5(j) and 11(d) are more active when compared to parent Fenretinide and other derivative compounds, indicating that these compounds can be used for: (i) combining radiotherapy with chemotherapy by labeling with I-131; and (ii) biodistribution studies by labeling with I-124 by combining it with PET imaging.

The flouro derivative compound, 5(h), can be synthesized with F18 isotope and can be used as an imaging agent. This molecule can be tested to determine if it is taken up by various tissues and tumors, by combining with PET studies.

Derivatives of 4-HPR were also obtained by changing both the peptide bond and the retinoic acid back bone; their cytotoxic activity was tested in a cell culture model of RTs. Changing the retinoic acid backbone does not change the activity of the compound consistent with the parallel finding that the phenyl group is the most active group for instilling cytotoxicity. Furthermore, derivatives of 4-HPR have been identified that are more active than the parent compound. The peptidomemitic derivatives are likely to be more stable in vivo. These findings indicate that these compounds are candidates for stable and active retinoic acid derivatives for use as anticancer drugs.

The results also demonstrate that down modulation of Cyclin D1 is a useful biological marker for determining the activities of the fenretinide derivative compounds and peptidomimetics against rhabdoid tumor cells. The activities of the fenretinide derivatives and peptidomimetics are directly correlated to their ability to down modulate Cyclin D1. These compounds, in addition, exhibited an increased ability to cause G1 phase cell cycle arrest. Interestingly, ATRA did not exhibit activities against rhabdoid tumor cells and it was unable to down modulate Cyclin D1. Furthermore, these compounds are of general interest for inhibiting survival of other tumor cell types.

REFERENCES

1. Garaventa A, Luksch R, Lo Piccolo M S, et al. Phase I trial and pharmacokinetics of fenretinide in children with neuroblastoma. Clin Cancer Res 2003; 9:2032-9.
2. Fontana J A, Rishi A K. Classical and novel retinoids: their targets in cancer therapy. Leukemia 2002; 16:463-72.
3. Formelli F, Camerini T, Cavadini E, et al. Fenretinide breast cancer prevention trial: drug and retinol plasma levels in relation to age and disease outcome. Cancer Epidemiol Biomarkers Prey 2003; 12:34-41.
4. Hail N, Jr., Kim H J, Lotan R. Mechanisms of fenretinide-induced apoptosis. Apoptosis 2006; 11:1677-94.
5. Zanardi S, Serrano D, Argusti A, Barile M, Puntoni M, Decensi A. Clinical trials with retinoids for breast cancer chemoprevention. Endocr Relat Cancer 2006; 13:51-68.
6. Bonanni B, Lazzeroni M, Veronesi U. Synthetic retinoid fenretinide in breast cancer chemoprevention. Expert Rev Anticancer Ther 2007; 7:423-32.
7. Lovat P E, Corazzari M, Di Sano F, Piacentini M, Redfern C P. The role of gangliosides in fenretinide-induced apoptosis of neuroblastoma. Cancer Lett 2005; 228:105-10.
8. Lovat P E, Corazzari M, Goranov B, Piacentini M, Redfern C P. Molecular mechanisms of fenretinide-induced apoptosis of neuroblastoma cells. Ann N Y Acad Sci 2004; 1028:81-9.
9. Reynolds C P. Detection and treatment of minimal residual disease in high-risk neuroblastoma. Pediatr Transplant 2004; 8 Suppl 5:56-66.
10. Reynolds C P, Matthay K K, Villablanca J G, Maurer B J. Retinoid therapy of high-risk neuroblastoma. Cancer Lett 2003; 197:185-92.
11. Bednarek A, Shilkaitis A, Green A, et al. Suppression of cell proliferation and telomerase activity in 4-(hydroxyphenyl)retinamide-treated mammary tumors. Carcinogenesis 1999; 20:879-83.
12. Bowman R, Clarke B, Duhig E, Larsen J, Fong K. Re: Effects of N-(4-hydroxy-phenyl)retinamide on hTERT expression in the bronchial epithelium of cigarette smokers. J Natl Cancer Inst 2002; 94:949-50; author reply 50-1.
13. Christov K, Ikui A, Shilkaitis A, et al. Cell proliferation, apoptosis, and expression of cyclin D1 and cyclin E as potential biomarkers in tamoxifen-treated mammary tumors. Breast Cancer Res Treat 2003; 77:253-64.
14. Delia D, Aiello A, Formelli F, et al. Regulation of apoptosis induced by the retinoid N-(4-hydroxyphenyl) retinamide and effect of deregulated bcl-2. Blood 1995; 85:359-67.
15. Hiyama K, Hiyama E. [Telomere and telomerase in lung cancer]. Nippon Rinsho 2002; 60 Suppl 5:737-42.
16. Igawa M, Tanabe T, Chodak G W, Rukstalis D B. N-(4-hydroxyphenyl) retinamide induces cell cycle specific growth inhibition in PC3 cells. Prostate 1994; 24:299-305.
17. Reynolds C P, Lemons R S. Retinoid therapy of childhood cancer. Hematol Oncol Clin North Am 2001; 15:867-910.
18. Soria J C, Moon C, Wang L, et al. Effects of N-(4-hydroxyphenyl)retinamide on hTERT expression in the bronchial epithelium of cigarette smokers. J Natl Cancer Inst 2001; 93:1257-63.
19. Soria J C, Xu X, Liu D D, et al. Retinoic acid receptor beta and telomerase catalytic subunit expression in bronchial epithelium of heavy smokers. J Natl Cancer Inst 2003; 95:165-8.
20. Sun S Y, Yue P, Kelloff G J, et al. Identification of retinamides that are more potent than N-(4-hydroxyphenyl)retinamide in inhibiting growth and inducing apoptosis of human head and neck and lung cancer cells. Cancer Epidemiol Biomarkers Prey 2001; 10:595-601.
21. Sun S Y, Yue P, Lotan R. Induction of apoptosis by N-(4-hydroxyphenyl)retinamide and its association with reactive oxygen species, nuclear retinoic acid receptors, and apoptosis-related genes in human prostate carcinoma cells. Mol Pharmacol 1999; 55:403-10.
22. Pirkmaier A, Yuen K, Hendley J, O'Connell M J, Germain D. Cyclin d1 overexpression sensitizes breast cancer cells to fenretinide. Clin Cancer Res 2003; 9:1877-84.
23. Christine Pratt M A, Niu M, White D. Differential regulation of protein expression, growth and apoptosis by natural and synthetic retinoids. J Cell Biochem 2003; 90:692-708.
24. DiPietrantonio A M, Hsieh T C, Olson S C, Wu J M. Regulation of G1/S transition and induction of apoptosis in HL-60 leukemia cells by fenretinide (4HPR). Int J Cancer 1998; 78:53-61.
25. Dragnev K H, Pitha-Rowe I, Ma Y, et al. Specific chemopreventive agents trigger proteasomal degradation of G1 cyclins: implications for combination therapy. Clin Cancer Res 2004; 10:2570-7.
26. Panigone S, Debernardi S, Taya Y, Fontanella E, Airoldi R, Delia D. pRb and Cdk regulation by N-(4-hydroxyphenyl)retinamide. Oncogene 2000; 19:4035-41.
27. Biegel J A. Molecular genetics of atypical teratoid/rhabdoid tumor. Neurosurg Focus 2006; 20:E11.
28. Alarcon-Vargas D, Zhang Z, Agarwal B, Challagulla K, Mani S, Kalpana G V. Targeting cyclin D1, a downstream effector of INI1/hSNF5, in rhabdoid tumors. Oncogene 2006; 25:722-34.
29. Tsikitis M, Zhang Z, Edelman W, Zagzag D, Kalpana G V. Genetic ablation of Cyclin D1 abrogates genesis of rhabdoid tumors resulting from Ini1 loss. Proc Natl Acad Sci U S A 2005; 102:12129-34.
30. Zhang Z K, Davies K P, Allen J, et al. Cell cycle arrest and repression of cyclin D1 transcription by INI1/hSNF5. Mol Cell Biol 2002; 22:5975-88.
31. Alvarez S, Germain P, Alvarez R, Rodriguez-Barrios F, Gronemeyer H, de Lera A R. Structure, function and modulation of retinoic acid receptor beta, a tumor suppressor. Int J Biochem Cell Biol 2007; 39:1406-15.
32. Dong S, Chen S J, Tweardy D J. Cross-talk between retinoic acid and STAT3 signaling pathways in acute promyelocytic leukemia. Leuk Lymphoma 2003; 44:2023-9.
33. Lefebvre P, Martin P J, Flajollet S, Dedieu S, Billaut X, Lefebvre B. Transcriptional activities of retinoic acid receptors. Vitam Horm 2005; 70:199-264.
34. Maden M. Retinoic acid in the development, regeneration and maintenance of the nervous system. Nat Rev Neurosci 2007; 8:755-65.
35. McCaffery P, Zhang J, Crandall J E. Retinoic acid signaling and function in the adult hippocampus. J Neurobiol 2006; 66:780-91.

36. Rawson N E, LaMantia A S. Once and again: retinoic acid signaling in the developing and regenerating olfactory pathway. J Neurobiol 2006; 66:653-76.
37. Soprano D R, Qin P, Soprano K J. Retinoic acid receptors and cancers. Arum Rev Nutr 2004; 24:201-21.
38. Njar V C, Gediya L, Purushottamachar P, et al. Retinoic acid metabolism blocking agents (RAMBAs) for treatment of cancer and dermatological diseases. Bioorg Med Chem 2006; 14:4323-40.
39. Chiesa F, Tradati N, Grigolato R, et al. Randomized trial of fenretinide (4-HPR) to prevent recurrences, new localizations and carcinomas in patients operated on for oral leukoplakia: long-term results. Int J Cancer 2005; 115:625-9.
40. Chiesa F, Tradati N, Marazza M, et al. Prevention of local relapses and new localisations of oral leukoplakias with the synthetic retinoid fenretinide (4-HPR). Preliminary results. Eur J Cancer B Oral Oncol 1992; 28B:97-102.
41. Decensi A, Fontana V, Fioretto M, et al. Long-term effects of fenretinide on retinal function. Eur J Cancer 1997; 33:80-4.
42. Decensi A, Torrisi R, Polizzi A, et al. Effect of the synthetic retinoid fenretinide on dark adaptation and the ocular surface. J Natl Cancer Inst 1994; 86:105-10.
43. Ferrari N, Morini M, Pfeffer U, Minghelli S, Noonan D M, Albini A. Inhibition of Kaposi's sarcoma in vivo by fenretinide. Clin Cancer Res 2003; 9:6020-9.
44. Finnegan C M, Blumenthal R. Fenretinide inhibits HIV infection by promoting viral endocytosis. Antiviral Res 2006; 69:116-23.
45. Guilbault C, De Sanctis J B, Wojewodka G, et al. Fenretinide Corrects Newly Found Ceramide Deficiency in Cystic Fibrosis. Am J Respir Cell Mol Biol 2007.
46. Krzeminski R, Zwas F, Esper P, Pienta K. Electroretinographic findings in subjects after administration of fenretinide. Doc Ophthalmol 1995; 91:299-309.
47. Lippman S M, Lee J J, Martin J W, et al. Fenretinide activity in retinoid-resistant oral leukoplakia. Clin Cancer Res 2006; 12:3109-14.
48. Lovat P E, Di Sano F, Corazzari M, et al. Gangliosides link the acidic sphingomyelinase-mediated induction of ceramide to 12-lipoxygenase-dependent apoptosis of neuroblastoma in response to fenretinide. J Natl Cancer Inst 2004; 96:1288-99.
49. Moglia D, Formelli F, Baliva G, et al. Effects of topical treatment with fenretinide (4-HPR) and plasma vitamin A levels in patients with actinic keratoses. Cancer Lett 1996; 110:87-91.
50. Myatt S S, Burchill S A. The sensitivity of the Ewing's sarcoma family of tumours to fenretinide-induced cell death is increased by EWS-Fli1-dependent modulation of p38(MAPK) activity. Oncogene. 2008 Feb. 7; 27(7):985-96. Epub 2007 August 13.
51. Ponthan F, Lindskog M, Karnehed N, Castro J, Kogner P. Evaluation of anti-tumour effects of oral fenretinide (4-HPR) in rats with human neuroblastoma xenografts. Oncol Rep 2003; 10:1587-92.
52. Ribatti D, Raffaghello L, Marimpietri D, et al. Fenretinide as an anti-angiogenic agent in neuroblastoma. Cancer Lett 2003; 197:181-4.
53. Saeed Z, Guilbault C, De Sanctis J B, et al. Fenretinide prevents the development of osteoporosis in Cftr-KO mice. J Cyst Fibros. 2008 May; 7(3):222-30. Epub 2007 November 7.
54. Takahashi N, Sausville E A, Breitman T R. N-(4-hydroxyphenyl)retinamide (Fenretinide) in combination with retinoic acid enhances differentiation and retinoylation of proteins. Clin Cancer Res 1995; 1:637-42.
55. Tradati N, Chiesa F, Rossi N, et al. Successful topical treatment of oral lichen planus and leukoplakias with fenretinide (4-HPR). Cancer Lett 1994; 76:109-11.
56. Vilela R M, Lands L C, Meehan B, Kubow S. Inhibition of IL-8 release from CFTR-deficient lung epithelial cells following pre-treatment with fenretinide. Int Immunopharmacol 2006; 6:1651-64.
57. Goodman A B. Retinoid receptors, transporters, and metabolizers as therapeutic targets in late onset Alzheimer disease. J Cell Physiol 2006; 209:598-603.
58. Yang Q, Graham T E, Mody N, et al. Serum retinol binding protein 4 contributes to insulin resistance in obesity and type 2 diabetes. Nature 2005; 436:356-62.
59. Racke M K, Burnett D, Pak S H, et al. Retinoid treatment of experimental allergic encephalomyelitis. IL-4 production correlates with improved disease course. J Immunol 1995; 154:450-8.
60. van Steensel M A. Emerging drugs for ichthyosis. Expert Opin Emerg Drugs 2007; 12:647-56.
61. Levine L. N-(4-hydroxyphenyl)retinamide: a synthetic analog of vitamin A that is a potent inhibitor of prostaglandin biosynthesis. Prostaglandins Med 1980; 4:285-96.
62. Orienti I, Zuccari G, Bergamante V, et al. Fenretinide-polyvinylalcohol conjugates: new systems allowing fenretinide intravenous administration. Biomacromolecules 2007; 8:3258-62.
63. Abou-Issa H, Curley R W, Jr., Alshafie G A, et al. Chemotherapeutic evaluation of 4-hydroxybenzylretinone (4-HBR), a nonhydrolyzable C-linked analog of N-(4-hydroxyphenyl)retinamide (4-HPR) against mammary carcinogenesis. Anticancer Res 2001; 21:3839-44.
64. Weiss K L, Alshafie G, Chapman J S, et al. An unhydrolyzable analogue of N-(4-hydroxyphenyl)retinamide. synthesis and preliminary biological studies. Bioorg Med Chem Lett 2001; 11:1583-6.
65. Liu S, Brown C W, Berlin K D, et al. Synthesis of flexible sulfur-containing heteroarotinoids that induce apoptosis and reactive oxygen species with discrimination between malignant and benign cells. J Med Chem 2004; 47:999-1007.
66. Winum J Y, Leydet A, Seman M, Montero J L. Synthesis and biological activity of glycosyl conjugates of N-(4-hydroxyphenyl)retinamide. Farmaco 2001; 56:319-24.
67. Villani M G, Appierto V, Cavadini E, et al. 4-oxo-fenretinide, a recently identified fenretinide metabolite, induces marked G2-M cell cycle arrest and apoptosis in fenretinide-sensitive and fenretinide-resistant cell lines. Cancer Res 2006; 66:3238-47.
68. Ahn J M, Boyle N A, MacDonald M T, Janda K D. Peptidomimetics and peptide backbone modifications. Mini Rev Med Chem 2002; 2:463-73.
69. Gentilucci L, Tolomelli A, Squassabia F. Peptides and peptidomimetics in medicine, surgery and biotechnology. Curr Med Chem 2006; 13:2449-66.
70. Perez J J, Corcho F, Llorens O. Molecular modeling in the design of peptidomimetics and peptide surrogates. Curr Med Chem 2002; 9:2209-29.
71. Reichelt A, Martin S F. Synthesis and properties of cyclopropane-derived peptidomimetics. Acc Chem Res 2006; 39:433-42.
72. Duguet E, Vasseur S, Mornet S, Devoisselle J M. Magnetic nanoparticles and their applications in medicine. Nanomed 2006; 1:157-68.

What is claimed is:

1. A compound having the structure:

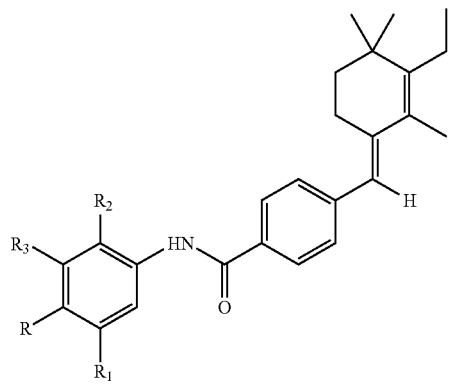

wherein R is OH;
wherein $R_1$, $R_2$ and $R_3$ are independently H, Br, Cl, I, F, alkyl, aryl, OH, $NO_2$, $NHR_4$, $OR_4$ or heterocyclic, where $R_4$ is alkyl, aryl or heterocyclic;
or a pharmaceutically acceptable salt thereof.

2. The compound of claim 1, wherein at least one of $R_1$, $R_2$ and $R_3$ is OH, Br, Cl, I or F, and wherein at least one of $R_1$, $R_2$ and $R_3$ is H.

3. The compound of claim 1, wherein at least one of $R_1$ and $R_3$ is Br, Cl, I or F.

4. The compound of claim 1, wherein $R_2$ is H or OH.

5. The compound of claim 1, wherein $R_3$ is I.

6. The compound of claim 1 having the structure:

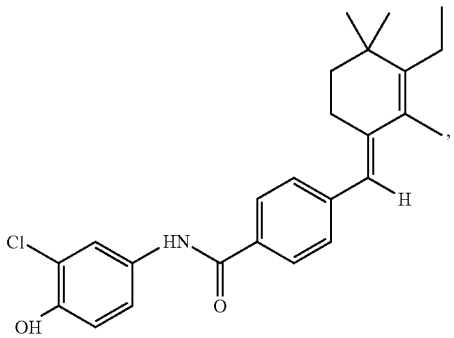 [SMILES: CCC1=C(C)/C(=C/c2ccc(C(=O)Nc3ccc(O)c(Cl)c3)cc2)CCC1(C)C]

or a pharmaceutically acceptable salt thereof.

7. The compound of claim 1 having the structure:

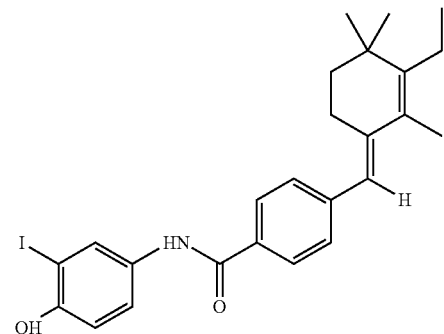 [SMILES: CCC1=C(C)/C(=C/c2ccc(C(=O)Nc3ccc(O)c(I)c3)cc2)CCC1(C)C]

or a pharmaceutically acceptable salt thereof.

8. The compound of claim 1 having the structure:

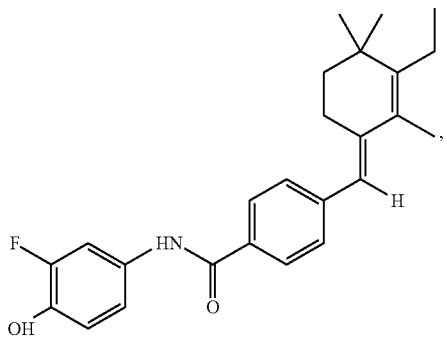 [SMILES: CCC1=C(C)/C(=C/c2ccc(C(=O)Nc3ccc(O)c(F)c3)cc2)CCC1(C)C]

or a pharmaceutically acceptable salt thereof.

9. The compound of claim 1, wherein the compound is radiolabeled.

10. The compound of claim 1, wherein the compound further comprises a nanoparticle conjugated to position R, $R_1$, $R_2$ or $R_3$.

11. A pharmaceutical composition comprising the compound of claim 1, and a pharmaceutically acceptable carrier or diluent.

12. A method of treating a subject having cancer comprising administering the compound of claim 1 to the subject in an amount and manner effective to treat cancer in the subject.

13. The method of claim 12, wherein the cancer is breast cancer, a rhabdoid tumor, a neuroblastoma, ovarian cancer, renal cancer, a malignant glioma or prostrate cancer.

14. A method of treating a subject having a disease comprising administering the compound of claim 1 to the subject in an amount and manner effective to treat the disease, wherein the disease is diabetes, AIDS, Alzheimer's Disease, cystic fibrosis, allergic encephalomyelitis or ichthyosis.

* * * * *